US011666391B2

(12) United States Patent
Rudie et al.

(10) Patent No.: US 11,666,391 B2
(45) Date of Patent: Jun. 6, 2023

(54) EXCITER ASSEMBLIES

(71) Applicant: Elucent Medical, Inc., Eden Prairie, MN (US)

(72) Inventors: Eric N. Rudie, Maple Grove, MN (US); Kassandra Klinkhammer, Eden Prairie, MN (US); Jason Hiltner, Eden Prairie, MN (US); Dave Costello, Eden Prairie, MN (US); Stan Kluge, Eden Prairie, MN (US); Lev Koyrakh, Eden Prairie, MN (US); Sean Morgan, Eden Prairie, MN (US); Daniel W. van der Weide, Madison, WI (US)

(73) Assignee: Elucent Medical, Inc., Eden Prairie, MN (US)

( * ) Notice: Subject to any disclaimer, the term of this patent is extended or adjusted under 35 U.S.C. 154(b) by 0 days.

(21) Appl. No.: 17/514,081

(22) Filed: Oct. 29, 2021

(65) Prior Publication Data

US 2022/0054203 A1 Feb. 24, 2022

Related U.S. Application Data

(63) Continuation of application No. 16/356,185, filed on Mar. 18, 2019, now Pat. No. 11,185,375, which is a
(Continued)

(51) Int. Cl.
*A61B 5/00* (2006.01)
*A61B 34/20* (2016.01)
(Continued)

(52) U.S. Cl.
CPC .............. *A61B 34/20* (2016.02); *A61B 5/002* (2013.01); *A61B 5/05* (2013.01); *A61B 5/062* (2013.01);
(Continued)

(58) Field of Classification Search
CPC combination set(s) only.
See application file for complete search history.

(56) References Cited

U.S. PATENT DOCUMENTS 3,689,885 A 9/1972 Kaplan et al.
3,706,094 A 12/1972 Cole et al.
(Continued)

FOREIGN PATENT DOCUMENTS

CN 101069640 11/2007
CN 102264292 11/2011
(Continued)

OTHER PUBLICATIONS

Li et al., Radio frequency identification technology: applications, technical challenges and strategies, Management Department Journal Article, 2006, paper 34, 28 pages.
(Continued)

*Primary Examiner* — Joel F Brutus
(74) *Attorney, Agent, or Firm* — Casimir Jones, S.C.; Brian F. Bradley

(57) ABSTRACT

Provided herein are systems, devices, assemblies, and methods for generating exciter signals, for example, to activate a remotely located tag. The systems, devices, assemblies, and methods find use in a variety of application including medical applications for the locating of a tag in a subject.

27 Claims, 16 Drawing Sheets

Related U.S. Application Data continuation of application No. 16/001,552, filed on Jun. 6, 2018, now Pat. No. 10,278,779.

(60) Provisional application No. 62/680,750, filed on Jun. 5, 2018.

(51) Int. Cl.
| | | |
|---|---|---|
| *A61B 5/06* | (2006.01) | |
| *A61B 90/00* | (2016.01) | |
| *A61B 5/05* | (2021.01) | |

(52) U.S. Cl.
CPC .............. *A61B 5/064* (2013.01); *A61B 90/39* (2016.02); *A61B 5/4312* (2013.01); *A61B 2034/2051* (2016.02); *A61B 2090/3908* (2016.02); *A61B 2090/3954* (2016.02); *A61B 2090/3958* (2016.02); *A61B 2505/05* (2013.01); *A61B 2562/0223* (2013.01); *A61B 2562/08* (2013.01)

(56) References Cited

U.S. PATENT DOCUMENTS

| | | |
|---|---|---|
| 4,494,545 A | 1/1985 | Slocum et al. |
| 4,561,443 A | 12/1985 | Hogrefe et al. |
| 4,804,054 A | 2/1989 | Howson et al. |
| 5,012,236 A | 4/1991 | Troyk et al. |
| 5,057,095 A | 10/1991 | Fabian |
| 5,095,309 A | 3/1992 | Troyk et al. |
| 5,142,292 A | 8/1992 | Chang |
| 5,198,807 A | 3/1993 | Troyk et al. |
| 5,221,831 A | 6/1993 | Geiszler et al. |
| 5,241,961 A | 9/1993 | Henry |
| 5,558,091 A | 9/1996 | Acker et al. |
| 5,752,513 A | 5/1998 | Acker et al. |
| 5,867,101 A | 2/1999 | Copeland et al. |
| 6,020,856 A | 2/2000 | Alicot |
| 6,026,818 A | 2/2000 | Blair et al. |
| 6,047,214 A | 4/2000 | Mueller et al. |
| 6,053,873 A | 4/2000 | Govari et al. |
| 6,069,564 A | 5/2000 | Hatano et al. |
| 6,073,043 A | 6/2000 | Schneider |
| 6,198,963 B1 | 3/2001 | Haim et al. |
| 6,249,212 B1 | 6/2001 | Beigel et al. |
| 6,263,247 B1 | 7/2001 | Mueller et al. |
| 6,361,532 B1 | 3/2002 | Burek |
| 6,363,940 B1 | 4/2002 | Krag |
| 6,499,488 B1 | 12/2002 | Hunter et al. |
| 6,675,810 B2 | 1/2004 | Krag |
| 6,698,433 B2 | 3/2004 | Krag |
| 6,765,476 B2 | 7/2004 | Steele et al. |
| 6,784,788 B2 | 8/2004 | Beigel et al. |
| 6,812,842 B2 | 11/2004 | Dimmer |
| 6,822,570 B2 | 11/2004 | Dimmer et al. |
| 6,838,990 B2 | 1/2005 | Dimmer |
| 6,889,833 B2 | 5/2005 | Seiler et al. |
| 6,977,504 B2 | 12/2005 | Wright et al. |
| 7,007,699 B2 | 3/2006 | Martinelli et al. |
| 7,023,391 B2 | 4/2006 | Wuidart et al. |
| 7,026,927 B2 | 4/2006 | Wright et al. |
| 7,135,978 B2 | 11/2006 | Gisselberg et al. |
| 7,174,201 B2 | 2/2007 | Govari et al. |
| 7,176,798 B2 | 2/2007 | Dimmer et al. |
| 7,289,839 B2 | 10/2007 | Dimmer et al. |
| 7,307,530 B2 | 12/2007 | Fabian et al. |
| 7,319,396 B2 | 1/2008 | Homanfar et al. |
| 7,347,379 B2 | 3/2008 | Ward et al. |
| 7,366,562 B2 | 4/2008 | Dukesherer et al. |
| 7,407,054 B2 | 8/2008 | Seiler et al. |
| 7,411,505 B2 | 8/2008 | Smith et al. |
| 7,414,404 B2 | 8/2008 | Keene |
| 7,420,468 B2 | 9/2008 | Fabian et al. |
| 7,474,223 B2 | 1/2009 | Nycz et al. |
| 7,518,518 B2 | 4/2009 | Homanfar et al. |
| 7,549,960 B2 | 6/2009 | Govari |
| 7,558,616 B2 | 7/2009 | Govari et al. |
| 7,575,550 B1 | 8/2009 | Govari |
| 7,590,441 B2 | 9/2009 | Govari et al. |
| 7,632,270 B2 | 12/2009 | Livneh |
| 7,657,301 B2 | 2/2010 | Mate et al. |
| 7,657,302 B2 | 2/2010 | Mate et al. |
| 7,657,303 B2 | 2/2010 | Mate et al. |
| 7,684,849 B2 | 3/2010 | Wright et al. |
| 7,696,876 B2 | 4/2010 | Dimmer et al. |
| 7,715,898 B2 | 5/2010 | Anderson |
| 7,747,307 B2 | 6/2010 | Wright et al. |
| 7,751,865 B2 | 7/2010 | Jascob et al. |
| 7,778,687 B2 | 8/2010 | Dimmer et al. |
| 7,814,916 B2 | 10/2010 | Revie et al. |
| 7,817,040 B2 | 10/2010 | Homanfar et al. |
| 7,818,044 B2 | 10/2010 | Dukesherer et al. |
| 7,840,253 B2 | 11/2010 | Tremblay et al. |
| 7,848,553 B2 | 12/2010 | Hertel et al. |
| 7,871,423 B2 | 1/2011 | Livneh |
| 7,899,513 B2 | 3/2011 | Phillips et al. |
| 7,912,529 B2 | 3/2011 | Herron et al. |
| 7,926,491 B2 | 4/2011 | Wright et al. |
| 7,971,341 B2 | 7/2011 | Dukesherer et al. |
| 7,993,335 B2 | 8/2011 | Rioux et al. |
| 8,011,508 B2 | 9/2011 | Seiler et al. |
| 8,012,154 B2 | 9/2011 | Livneh |
| 8,057,407 B2 | 11/2011 | Martinelli et al. |
| 8,057,468 B2 | 11/2011 | Konesky |
| 8,100,897 B2 | 1/2012 | Zoran |
| 8,113,210 B2 | 2/2012 | Petcavich et al. |
| 8,114,181 B2 | 2/2012 | Gogolin |
| 8,196,589 B2 | 6/2012 | Gisselberg et al. |
| 8,226,640 B2 | 7/2012 | Zoran |
| 8,239,001 B2 | 8/2012 | Verard et al. |
| 8,271,069 B2 | 9/2012 | Jascob et al. |
| 8,354,837 B2 | 1/2013 | Anderson |
| 8,359,730 B2 | 1/2013 | Burg et al. |
| 8,377,388 B2 | 2/2013 | Konesky |
| 8,399,837 B2 | 3/2013 | Robbins et al. |
| 8,409,190 B2 | 4/2013 | Konesky et al. |
| 8,467,852 B2 | 6/2013 | Csavoy et al. |
| 8,549,732 B2 | 10/2013 | Burg et al. |
| 8,628,524 B2 | 1/2014 | Shilev |
| 8,644,907 B2 | 2/2014 | Hartmann et al. |
| 8,647,342 B2 | 2/2014 | Livneh |
| 8,696,663 B2 | 4/2014 | Pardoll et al. |
| 8,728,076 B2 | 5/2014 | Livneh |
| 8,795,265 B2 | 8/2014 | Konesky et al. |
| 8,795,272 B2 | 8/2014 | Rioux et al. |
| 8,802,022 B2 | 8/2014 | Konesky |
| 8,830,037 B2 | 9/2014 | Burke et al. |
| 8,857,043 B2 | 10/2014 | Dimmer et al. |
| 8,892,185 B2 | 11/2014 | Chi Sing et al. |
| 8,939,153 B1 | 1/2015 | Reicher et al. |
| 8,948,845 B2 | 2/2015 | Glossop et al. |
| 8,968,171 B2 | 3/2015 | Mckenna et al. |
| 8,973,584 B2 | 3/2015 | Brander et al. |
| 8,979,834 B2 | 3/2015 | Zoran et al. |
| 8,998,899 B2 | 4/2015 | Shilev et al. |
| 9,002,434 B2 | 4/2015 | Uchiyama et al. |
| 9,060,765 B2 | 6/2015 | Rencher et al. |
| 9,095,333 B2 | 8/2015 | Konesky et al. |
| 9,144,453 B2 | 9/2015 | Rencher et al. |
| 9,234,877 B2 | 1/2016 | Hattersley et al. |
| 9,239,314 B2 | 1/2016 | Hattersley et al. |
| 9,730,764 B2 | 8/2017 | Van Der Weide et al. |
| 9,987,097 B2 | 6/2018 | Van Der Weide et al. |
| 10,154,799 B2 | 12/2018 | Van Der Weide et al. |
| 10,245,118 B2 | 4/2019 | Van Der Weide et al. |
| 10,245,119 B2 | 4/2019 | Van Der Weide et al. |
| 10,278,779 B1 | 5/2019 | Rudie et al. |
| 2002/0040185 A1* | 4/2002 | Atalar .................. A61B 5/4381 600/423 |
| 2003/0018246 A1 | 1/2003 | Govari et al. |
| 2003/0117269 A1 | 6/2003 | Dimmer |
| 2003/0153850 A1 | 8/2003 | Davis et al. |
| 2004/0093187 A1 | 5/2004 | Dames et al. |
| 2004/0123871 A1 | 7/2004 | Wright et al. |

(56) References Cited

U.S. PATENT DOCUMENTS

| | | |
|---|---|---|
| 2004/0169505 A1 | 9/2004 | Alun et al. |
| 2004/0199067 A1 | 10/2004 | Bock et al. |
| 2006/0093089 A1 | 5/2006 | Vertatschitsch et al. |
| 2007/0135803 A1 | 6/2007 | Belson |
| 2007/0232882 A1 | 10/2007 | Glossop et al. |
| 2008/0119919 A1 | 5/2008 | Atalar |
| 2008/0125630 A1 | 5/2008 | Caylor |
| 2008/0132860 A1 | 6/2008 | Smith et al. |
| 2008/0194912 A1 | 8/2008 | Trovato et al. |
| 2008/0213382 A1 | 9/2008 | Ivkov et al. |
| 2008/0281190 A1 | 11/2008 | Petcavich et al. |
| 2009/0009335 A1 | 1/2009 | Stewart et al. |
| 2009/0216113 A1* | 8/2009 | Meier .................. A61B 90/39 600/424 |
| 2009/0281419 A1 | 11/2009 | Troesken et al. |
| 2010/0004523 A1 | 1/2010 | August et al. |
| 2010/0274145 A1 | 10/2010 | Tupin et al. |
| 2010/0275934 A1 | 11/2010 | Keren |
| 2010/0305430 A1 | 12/2010 | Troesken et al. |
| 2011/0152673 A1 | 6/2011 | Doerr et al. |
| 2011/0152677 A1 | 6/2011 | Faul |
| 2011/0201923 A1 | 8/2011 | Shen |
| 2011/0278948 A1 | 11/2011 | Forsell |
| 2012/0082342 A1 | 4/2012 | Kim et al. |
| 2013/0052953 A1 | 2/2013 | Rofougaran |
| 2013/0237982 A1 | 9/2013 | Rencher et al. |
| 2013/0345561 A1 | 12/2013 | Quigley |
| 2014/0018663 A1 | 1/2014 | Harmer et al. |
| 2014/0062717 A1 | 3/2014 | Mudumbai et al. |
| 2014/0066754 A1 | 3/2014 | Chi Sing et al. |
| 2014/0148692 A1 | 5/2014 | Hartmann et al. |
| 2014/0309522 A1 | 10/2014 | Fullerton et al. |
| 2015/0100109 A1 | 4/2015 | Feldman et al. |
| 2015/0129664 A1 | 5/2015 | Brar |
| 2015/0141811 A1 | 5/2015 | Ritchey et al. |
| 2015/0196369 A1 | 7/2015 | Glossop et al. |
| 2015/0264891 A1 | 9/2015 | Brander et al. |
| 2016/0022216 A1 | 1/2016 | Goldshtein et al. |
| 2016/0051164 A1 | 2/2016 | Derichs et al. |
| 2016/0192960 A1 | 7/2016 | Bueno et al. |
| 2017/0007352 A1 | 1/2017 | Van Der Weide et al. |
| 2017/0095313 A1 | 4/2017 | Van Der Weide et al. |
| 2017/0095315 A1* | 4/2017 | van der Weide ...... A61B 90/98 |
| 2017/0098149 A1 | 4/2017 | Kesler |
| 2017/0238996 A1 | 8/2017 | Frame et al. |
| 2017/0312046 A1 | 11/2017 | Van Der Weide et al. |
| 2018/0353259 A1 | 12/2018 | Van Der Weide et al. |
| 2019/0090779 A1 | 3/2019 | Van Der Weide et al. |
| 2019/0209263 A1 | 7/2019 | Van Der Weide et al. |
| 2019/0239980 A1 | 8/2019 | Van Der Weide et al. |
| 2019/0365478 A1 | 12/2019 | Rudie et al. |

FOREIGN PATENT DOCUMENTS

| | | |
|---|---|---|
| DE | 10112303 | 10/2002 |
| DE | 102011006537 | 10/2012 |
| EP | 1232730 | 8/2002 |
| JP | 2012-524627 | 10/2012 |
| WO | WO 1993/005707 | 4/1993 |
| WO | WO 2007/064013 | 6/2007 |
| WO | WO 2010/058150 | 5/2010 |
| WO | WO 2010/124117 | 10/2010 |
| WO | WO 2015039039 | 3/2015 |
| WO | WO 2015/063280 | 5/2015 |
| WO | WO 2015112863 | 1/2016 |
| WO | WO 2017059228 | 4/2017 |
| WO | WO 2018/031826 | 2/2018 |
| WO | WO 2019/236600 | 12/2019 |

OTHER PUBLICATIONS

Luini et al., Comparison of Radioguided excision with wire localization of occult breast lesions, Br. J. Surg, 1999, 86:522-525.

Mickle et al., Intellecutual Property and Ubiquitos RFID, Recent Patents on Electrical Engineering, 2008, 1:59-67.

Radio Frequency Identification: Opportunites and Challenges in Immpementation, Department of Commerce, 2005, Washington D.C., 38 pages.

Shah et al, Expanding the use of real-time electromagnetic tracking in radiation oncology, J Appl Clin Med Phys. Nov. 15, 2011; 12(4):3590.

Shantz, A Near Field Propagation Law & A Novel Fundamental Limit to Antenna Gain Versus Size. Antennas and Propagation Society International Symposium, 2005 IEEE, Jul. 3-8, 2005, Washington D.C. 4 pages.

Soon, Radio Frequency Identification History and Development, Chapt. 1, Ubiquitous and Pervasive Computing: Concepts, Methodologies, Tools, and Applications, 2010, ed. Symonds, 17 pages.

Stockman, Communication by Means of Reflected Power, Proceedings of the I.R.E., 1948, 36(10):1196-1204.

Takahata et al., Thoracoscopic surgery support system using passive RFID marker, 34th Annual International Conference of the IEEE EMBS, San Diego, CA, Aug. 28-Sep. 1, 2012, pp. 183-186.

Van Lieshout et al., RFID Technologies: Emerging Issues, Challenges and Policy Options, JRC Scientific and Technical Reports, 2007, 278 pages.

Want, RFID: A Key to Automating Everything, Scientific American, Inc., Jan. 2004, pp. 56-63.

International Search Report and Written Opinion, dated May 5, 2016, for PCT/US2015/012687, 11 pages.

International Search Report and Written Opinion for PCT/US2016/054738, dated Jan. 31, 2017, 9 pages.

European Supplemental Search Report for EP15740262.9, dated Sep. 18, 2017, 14 pages.

International Search Report and Written Opinion for PCT/US2017/046379, dated Dec. 5, 2017, 15 pages.

European Supplemental Search Report for EP16852699.4, dated May 10, 2019, 10 pages.

International Search Report and Written Opinion for PCT/US2019/035424, dated Oct. 24, 2019, 13 pages.

European Search Report for EP17840310.1, dated Mar. 30, 2020, 11 pages.

Liehr, Sascha (2006) Optical Measurement of Currents in Power Converters.

Alain, Tran & Bolic, Miodrag & Yagoub, Mustapha. 2010 Magnetic-Filed Coupling Characteristics of Ferrite-Coil Antennas for Low-Frequency RFID Applications. International Journal of Computer Science Issues. 7.

Applications of ferrite core inductors. Semiconductor for You. Jul. 25, 2007. Retrieved Feb. 28, 2022, from https://www.semiconductorforu.com/applications-ferrite-core-inductors/.

* cited by examiner

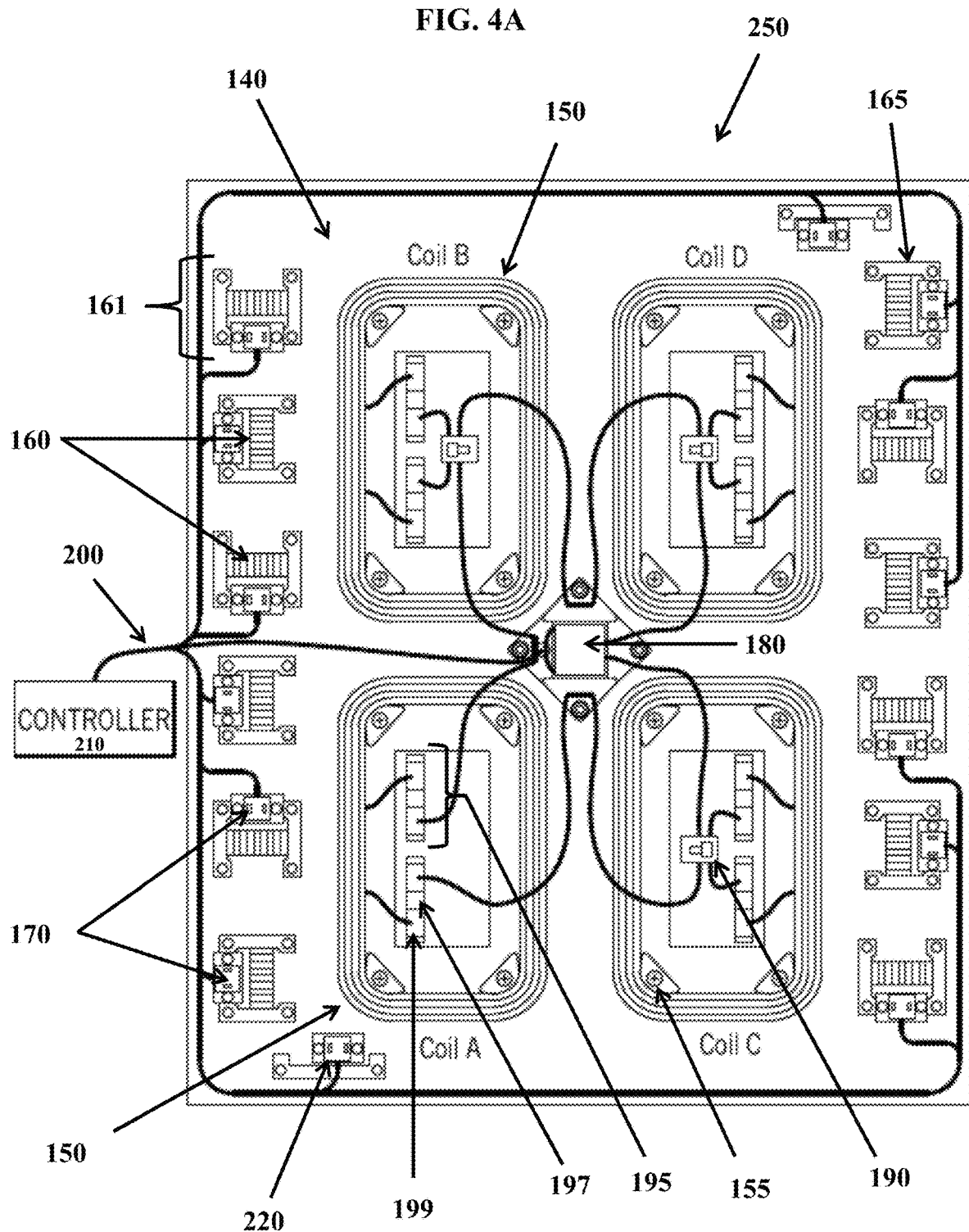

EXCITER ASSEMBLIES

The present application is a continuation of U.S. patent application Ser. No. 16/356,185, filed Mar. 18, 2019, which is a continuation of U.S. patent application Ser. No. 16/001,552, filed Jun. 6, 2018, issued as U.S. Pat. No. 10,278,779, which claims priority to U.S. Provisional Application Ser. No. 62/680,750 filed Jun. 5, 2018, each of which is herein incorporated by reference in its entirety.

FIELD

Provided herein are systems, devices, assemblies, and methods for generating exciter signals, for example, to activate a remotely located marker tag. The systems, devices, assemblies, and methods find use in a variety of applications including medical applications for the locating of a tag in a subject.

BACKGROUND

A common and serious challenge for many medical procedures is the accurate localization of treatment areas. For example, the location of lesions, such as tumors that are to undergo treatment, including surgical resection, continues to present a challenge to the medical community. Existing systems are expensive, complex, time-consuming, and often unpleasant for the patient. Such issues are illustrated by the surgical treatment of breast lesions.

A common technique used in breast tumor surgery is wire localization of the lesions. Precise preoperative localization of some breast lesions is necessary before removal of the lesion. Wire localization is used to mark the location of a breast abnormality. The procedure ensures greater accuracy for a breast biopsy or lumpectomy. The surgeon typically uses the wire as a guide to the tissue that needs to be removed. Wire localization is typically conducted in the radiology department of the hospital or surgical center. Mammograms (or in some cases, ultrasound images) are taken to show the location of the breast abnormality. Patients are awake during the placement of the wire, but the breast tissue is numbed to reduce or avoid pain from the needle or the wire. It is possible to feel pressure or pulling sensations during the wire placement. Once images have been taken, and the tissue has been numbed, the radiologist will use a needle to target the breast abnormality. The tip of this needle rests in the location that the surgeon needs to find in order to remove the right tissue. A slender wire is threaded down through the needle and out of its tip, to lodge at the target tissue. The needle is removed, leaving the wire in place. With the wire in place, the patient has another mammogram, to check that the tip of the wire is properly positioned. If the wire is not in the correct place, the radiologist will reposition and re-check it, to ensure accurate placement. When the wire is finally positioned, it will be secured in place with tape or a bandage. The wire localization procedure can take about an hour, and is usually scheduled hours before biopsy or lumpectomy. Thus, the patient must often wait hours for surgery with the wire present in their body and protruding from their skin. The wire is removed, along with some breast tissue, during surgery. This process takes many hours, involves multiple imaging steps, and is inconvenient and unpleasant for the patient—as well as being expensive.

A similar type of procedure is done to localize pulmonary nodules prior to resection. In some cases where pulmonary nodules may be difficult to locate at conventional open surgery or at thoracoscopy, a hook wire, injection of visible dye, or a radionuclide is placed in or around the nodule in an attempt to improve localization prior to removal. This procedure usually takes place in the computerized tomography (CT) suite prior to the removal of the nodule. The patient is then transported to the surgical unit and the surgeon cuts down on the wire, uses a radionuclide detector, or uses visual landmarks to localize and remove the nodule.

In other types of surgeries and medical procedures, physicians may have trouble locating a target prior to removal or manipulation. Examples of this include the removal of masses, fluid collections, foreign bodies or diseased tissues. Other times, placements of catheters or other percutaneous procedures are performed either without direct visualization or with the lack of a specific guidance modality. Performing procedures without precise guidance can increase the amount of damage to normal tissues and decrease the patient's functional status.

Percutaneous biopsy is a well-accepted, safe procedure performed in virtually every hospital. Biopsy often entails placement of a co-axial guide needle through which the biopsy device is placed into the target. Many of the lesions that are removed, punctured or manipulated as described above have previously undergone successful percutaneous biopsy. The placement of the guide needle for biopsy is an opportunity to place a fiduciary or other localizing system without causing additional tissue trauma than the patient would otherwise undergo.

Many other medical devices and procedures could benefit from improved tissue localization. These include any procedure or test that is degraded by any bodily motion such as cardiac motion, respiratory motion, motion produced by the musculoskeletal system, or gastrointestinal/genitourinary motion. Examples of these include external beam radiation therapy, placement of brachytherapy seeds, imaging tests including but not limited to CT, MRI, fluoroscopy, ultrasound, and nuclear medicine, biopsies performed in any fashion, endoscopy, laparoscopic and thoracoscopic surgery and open surgical procedures.

Improved systems and methods are needed for tissue localization for medical procedures.

SUMMARY

Provided herein are systems, devices, assemblies, and methods for generating exciter signals, for example, to activate a remotely located tag. The systems, devices, assemblies, and methods find use in a variety of applications including medical applications for the locating of a tag in a subject. While the description below illustrates the invention using examples of human surgical procedures, it should be appreciated that the invention is not so limited and includes veterinary applications, agricultural applications, industrial applications, mechanical applications, military applications (e.g., sensing and removal of dangerous materials from an object or region), aerospace applications, and the like.

In some embodiments, provided herein are systems comprising one or more or each of: a) one or more tags; b) a remote activation device (e.g., exciter assembly) that generates a magnetic field (e.g., time varying magnetic field) within a region of the tag, the remote activating device comprising four or more exciter coils each configured to flow current in either a clockwise or counterclockwise direction such that the magnetic field generated by the remote activating device may be selectively generated in substantially any of X, Y, or Z directions (e.g., to ensure that the tag(s) can be excited for any angle that it may be placed); and c) a plurality of sensors configured to detect a signal from the one or more tags when the one or more tags is exposed to the magnetic field. In some embodiments, the four or more exciter coils are connected in series. In some embodiments, four of the exciter coils are in a layout of two rows centered at coordinates (X1, Y1), (X1, Y2), (X2, Y1), and (X2, Y2). In some embodiments, the remote activating device (e.g., exciter assembly) comprises three current flow configurations: a) all current clockwise to simulate an exciter coil aligned with a direction normal to the Z axis; b) exciter coils centered at (X2, Y1), (X2, Y2) running current counter-clockwise to simulate an exciter coil aligned to the X axis; and c) exciter coils centered at (X1, Y2), (X2, Y2) running current counter-clockwise to simulate an exciter coil aligned substantially to the Y axis. In some embodiments, the remote activating device (e.g., exciter assembly) comprises a plurality of relays that provide a switching function to accomplish the current direction change (polarity) yet maintain an excitation frequency by switching additional capacitive reactance. In some embodiments, the switching function inserts additional series capacitive reactance via a capacitance element when total inductance is increased so that a tuning center frequency is maintained at said excitation frequency (e.g., the total inductance of the 4 coils, when 4 coils are employed, varies as the current direction is changed within each coil or coil pair). In some embodiments, the capacitance element is comprised of multiple capacitors (e.g., to better accommodate the voltage potential at resonance and/or to provide greater flexibility on frequency tuning). In some embodiments, the remote activating device further comprises a balun in proximity to the exciter coils. The balun eliminates common mode current that would otherwise produce unwanted electric field components that could otherwise reduce accuracy. It also provides impedance transformation to match the real component of the coil impedance to that of the transmission line, typically 50 Ohms. In some embodiments, the balun has eight turns on a primary side (amplifier side) and four turns on a secondary side (coil side). In some embodiments, the system further comprises an amplifier in electronic communication with the remote activating device. In some embodiments, the system further comprises a computer that controls magnetic field generation and sensor detection. In some embodiments, the computer comprises a hunting algorithm (e.g., embodied in software running on the processor) that adjusts the magnetic field orientation to identify (and power) optimal detection of one or more tags.

Also provided herein are uses of any of the above systems (e.g., for detecting a position of a tag in an object; for detecting a position of a tag relative to a medical device; etc.).

Further provided herein are methods of identifying a position of a tag, comprising: a) providing any of the systems described herein; b) placing the tag in an object; c) generating a magnetic field with the activating device; and d) identifying a position of said tag in said object by collecting information emitted from the tag with the witness stations. In some embodiments, the position or comprises relative location or distance of the tag to a medical device.

In certain embodiments, provided herein are systems and devices comprising: an exciter assembly that cycles between generating at least first, second, and third magnetic fields (e.g., first, second, third, fourth, fifth, sixth, seventh, and/or eighth magnetic fields) for causing a tag to generate a signal, wherein the exciter assembly comprises A) a base substrate, B) a first exciter coil attached to the base substrate, wherein current in the first exciter coil travels clockwise when the first, second, and third magnetic fields are generated, C) a second exciter coil attached to base substrate, wherein current in the second exciter coil travels clockwise when the first and second magnetic fields are generated, and travels counterclockwise when the third magnetic field is generated, D) a third exciter coil attached to the base substrate, wherein current in the third exciter coil travels clockwise when the first and third magnetic fields are generated, and travels counterclockwise when the second magnetic field is generated; and E) a fourth exciter attached to the base substrate, wherein current in the fourth exciter coil travels clockwise when the first magnetic fields is generated, and travels counterclockwise when the second and third magnetic fields are generated.

Exciter coils, for example, may be wound using Litz wire to minimize resistive losses due to the skin effect that occurs as frequency increases. The number of turns is generally chosen to maximize coil "Q" (the ratio of inductance/resistance). An exemplary coil example is 63 turns of Litz wire comprised of 100 strands of 38 AWG wire. Inductance of an individual coil measures about 1.1 mH and Q (ratio of inductive reactance to resistance) measures over 500 at 134.5 KHz. Other coil constructions using other wire with different values of inductance and Q may be used. However, it is generally desired to keep "Q" as high as possible to minimize resistive losses that result in loss of efficiency and greater thermal heating.

In some embodiments, provided herein are systems and devices comprising: a) a base substrate, b) first, second, third, and fourth exciter coils attached to the substrate and configured to generate a magnetic field for causing a tag to generate a signal, c) a balun circuit electrically linked to the first, second, third, and fourth exciter coils.

In particular embodiments, each of the second, third, and fourth exciter coils are operatively connected to a switch that controls the direction of current through a coil. In certain embodiments, each switch comprises a relay element, a PIN diode, a Field Effect Transistor, or other solid state switching device. In particular embodiments, each switch additionally switches at least one capacitor (e.g., two capacitors) into the circuit to keep the resonant frequency of the series combination of exciter coils constant regardless of the change in overall coil inductance that results from changing coil polarity.

The inductance of an exemplary exciter coil system measures 1.1 mH with Q>500 for each individual coil. The inductance of the series combination of 4 coils (e.g., as shown in FIG. 4A) varies with polarity (current direction) of the coils because of the interaction of the magnetic flux produced by each coil. The inductance of the series combination of all 4 exemplary coils measures 3.9 mH with Q=435 for the current direction depicted in FIG. 5 where all coils have current flowing in the clockwise direction. The inductance of the series combination of all 4 exemplary coils measures 4.6 mH with Q=500 for the current direction depicted in FIG. 6 where coils A and B have current in the clockwise direction and coils C and D have current flowing in the counterclockwise direction. The inductance of the series combination of all 4 exemplary coils measures 4.3 mH with Q=473 for the current direction depicted in FIG. 7 where coils A and C have current in the clockwise direction and coils B and D have current flowing in the counterclockwise direction. This variation in total inductance necessitates switching in appropriate compensation capacitors when the coil polarity is changed.

In some embodiments, the components of the relay or switch and associated capacitors may be placed on a ceramic substrate to provide secure mounting, excellent dielectric properties, and also serve as a heat spreader to reduce localized heating of individual components.

In some embodiments, the systems and devices further comprise: a plurality of witness coils or witness station assemblies attached to the substrate and configured to detect the signal from the tag. In some embodiments, the witness coils are placed such that the axis of the coil is co-planar with the central plane of the exciter coils. In this plane, the magnetic flux produced by the exciter is orthogonal to the sensing axis of the witness coils for every combination of coil current direction described previously. The orthogonal exciter current does not induce a signal into the witness coils and thus provides isolation between the exciter coil and witness coils. This isolation is generally needed to achieve the needed system dynamic range so that the very weak tag signal may be detected in the presence of the very large exciter magnetic field. This isolation is also important because crosstalk between the exciter coil and witness coils would otherwise greatly impede navigation because the crosstalk term would contribute significant signal arising from the same magnetic dipole (the exciter) to all witness coils and therefore the witness coils would lose their spatial independence. An additional point is that the presence of the z-oriented exciter significantly distorts the z-component of the tag (and emitter) magnetic field, making it less useful for navigation.

In further embodiments, the plurality of witness coils, or plurality of witness station assemblies, comprises six to thirty witness coils (e.g., 6 . . . 9 . . . 12 . . . 20 . . . or 30). In additional embodiments, the plurality of witness coils: i) are located on opposing sides of said base substrate, but not adjacent to said opposing sides, and/or ii) are each positioned to alternate opposite orientation along x and y axes with respect to other witness coils. This positioning minimizes crosstalk between witness coils and thereby reduces the degree that crosstalk compensation that is applied (e.g., by a mathematic solver software).

In some embodiments, the systems and devices further comprise a plurality of printed circuit boards, wherein each of the plurality of witness coils is operably linked to one of the plurality of circuit boards. In certain embodiments, each circuit board comprises at least two capacitors and at least one balun circuit. In particular embodiments, the systems and devices further comprise the tag.

In certain embodiments, the systems and devices further comprise a balun circuit that is electrically linked to the first, second, third, and fourth exciter coils. In further embodiments, the systems and devices further comprise a cable bundle that is electrically linked to the balun circuit. In additional embodiments, the systems and devices further comprise a plurality of witness coils attached to the substrate and configured to detect the signal from the tag, wherein the plurality of witness coils are electrically linked to the cable bundle.

In some embodiments, the systems and devices further comprise at least one self-test emitter. In other embodiments, the systems and methods further comprise a top cover, wherein the top cover mates with the base substrate to enclose the first, second, third, and fourth exciter coils therein.

In other embodiments, the systems and devices further comprise a system electronics enclosure which is configured to provide a signal to the first, second, third, and fourth exciter coils. In other embodiments, the center of each of the first, second, third, and fourth exciter coils is separated from each other by at least 5 centimeters (e.g., 5 . . . 10 . . . 15 . . . 25 . . . 100 . . . 1000 cm). In other embodiments, the center of each of the first, second, third, and fourth exciter coils is separated from each other by 2-5 times the largest dimension of the coils themselves. In certain embodiments, the fourth exciter coil is positioned next to the second exciter coil, and wherein the third exciter coil is positioned next to the first exciter coil and diagonal from the second exciter coil.

In some embodiments, provided herein are methods comprising: a) positioning the systems or devices disclosed herein below or near a patient that has a tag located therein, and b) activating the system or device such that an magnetic field is generated, thereby causing the tag to generate a signal.

In some embodiments, provided herein are systems and devices comprising a witness station assembly, wherein the witness station assembly comprises: a) a witness coil, wherein the witness coil comprises: i) a metal core having a coil-free proximal end, a coil-free distal end, and a central region, and ii) coil windings wound around the central region of the metal core, b) first and second witness coil brackets, and c) first and second elastomeric parts, wherein the coil-free proximal end of the metal core is secured between the first witness coil bracket and the first elastomeric part, and wherein the coil-free distal end of the metal core is secured between the second witness coil bracket and the second elastomeric part. In certain embodiments the systems or devices further comprise a remote activation device (e.g., as described herein), wherein the remote activation device comprises at least one exciter coil. In further embodiments, the systems and devices further comprise: an exciter assembly (e.g., as described herein), wherein the exciter assembly comprises at least one exciter coil.

In further embodiments, the first and second witness coil brackets each comprises at least one adjustment part (e.g., two adjustment screws). In some embodiments, the at least one adjustment part comprises at least one screw and/or at least one rod. In other embodiments, the witness station assembly further comprises an electronics part electrically linked to the witness coil. In other embodiments, the electronics part comprises at least one capacitor and/or at least one balun circuit. In further embodiments, the electronics part comprises a printed circuit board. In certain embodiments, the witness station assembly further comprises a faraday shield.

In other embodiments, the witness station assembly further comprises: i) an electronics part electrically linked to said witness coil, and ii) a faraday shield. In additional embodiments, the first and second elastomeric parts comprise a material selected from: an elastomer polymer and a spring.

In some embodiments, the metal core comprise a ferrite core. In other embodiments, the metal core has a diameter of 4 to 25 mm (4 . . . 8 . . . 12 . . . 14 . . . 16 . . . 25 mm). In certain embodiments, the metal core has a length of 15 to 75 mm (e.g., 15 . . . 30 . . . 45 . . . 58 . . . 75 mm). In particular embodiments, the coil windings comprise metal wire. In other embodiments, the metal wire is wound around said metal core 150-300 times. In further embodiments, the first and second witness coil brackets each comprises a notch configured to fit the wire-free proximal end and/or the wire-free distal end of said metal core.

In particular embodiments, provided herein are devices and systems comprising: a) an attachment component (e.g., a sheath) configured to be attached to a hand-held medical device with a device tip, wherein the attachment component comprises: i) a proximal end, ii) an angled distal end, wherein the angled distal end comprises a distal end opening configured to allow the device tip, but not the remainder of the medical device, to pass therethrough, and iii) a main body stretching between the proximal end and the angled distal end, and b) first and second location emitters attached to the attachment component.

In certain embodiments, the angled distal end has an angle of at least 35 degrees with respect to the longitudinal axis of the attachment component (e.g., at least 35 . . . 45 . . . 65 . . . 85 . . . or 95 degrees). In some embodiments, the angled distal end has an angle of about 90 degrees with respect to the longitudinal axis of the attachment component. In further embodiments, the first and second location emitters are attached to the main body of the attachment component (e.g., spaced apart).

In other embodiments, systems and devices further comprise: c) a display component housing, wherein the display component housing is attached to, or attachable to, the proximal end of the attachment component. In additional embodiments, the systems and devices further comprise a display component attached to the display component housing, wherein the display component comprises a display screen (e.g., LCD screen) for displaying the location of an implanted tag in a patient relative to the device tip on a medical device. In other embodiments, the display component housing comprises a cable management component. In additional embodiments, the display component housing comprises a housing tapered connection. In further embodiments, the proximal end of the attachment component comprises a proximal tapered connection.

In other embodiments, the devices and systems further comprise first and second location emitter wire leads, wherein the first location emitter wire lead is electrically linked to the first location emitter (e.g., small coil), and the second location emitter wire lead is electrically linked to the second location emitter (e.g., small coil). In other embodiments, the systems and devices further comprise: c) an adhesive strip sized and shaped to cover at least 50% (e.g., 50% . . . 75% . . . 90%) of the attachment component main body, and configured to adhere the attachment component to the medical device. In certain embodiments, the systems and devices further comprise: c) the medical device. In other embodiments, the medical device comprises an electrocautery surgical device.

Definitions

As used herein, the terms "processor" and "central processing unit" or "CPU" are used interchangeably and refer to a device that is able to read a program from a computer memory (e.g., ROM or other computer memory) and perform a set of steps according to the program.

As used herein, the terms "computer memory" and "computer memory device" refer to any storage media readable by a computer processor. Examples of computer memory include, but are not limited to, RAM, ROM, computer chips, digital video discs (DVD), compact discs (CDs), hard disk drives (HDD), optical discs, and magnetic tape. In certain embodiments, the computer memory and computer processor are part of a non-transitory computer (e.g., in the control unit). In certain embodiments, non-transitory computer readable media is employed, where non-transitory computer-readable media comprises all computer-readable media with the sole exception being a transitory, propagating signal.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks, whether local or distant (e.g., cloud-based).

As used herein, the term "in electronic communication" refers to electrical devices (e.g., computers, processors, etc.) that are configured to communicate with one another through direct or indirect signaling. Likewise, a computer configured to transmit (e.g., through cables, wires, infrared signals, telephone lines, airwaves, etc.) information to another computer or device, is in electronic communication with the other computer or device.

As used herein, the term "transmitting" refers to the movement of information (e.g., data) from one location to another (e.g., from one device to another) using any suitable means.

As used herein, the term "subject" or "patient" refers to any animal (e.g., a mammal), including, but not limited to, humans, non-human primates, companion animals, livestock, equines, rodents, and the like, which is to be the recipient of a particular treatment. Typically, the terms "subject" and "patient" are used interchangeably herein in reference to a human subject.

As used herein, the term "subject/patient suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass) but for whom the stage of cancer is not known. The term further includes people who once had cancer (e.g., an individual in remission).

As used herein, the term "biopsy tissue" refers to a sample of tissue (e.g., breast tissue) that is removed from a subject for the purpose of determining if the sample contains cancerous tissue. In some embodiments, biopsy tissue is obtained because a subject is suspected of having cancer. The biopsy tissue is then examined (e.g., by microscopy; by molecular testing) for the presence or absence of cancer.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include tissue, blood products, such as plasma, serum and the like. Such examples are not however to be construed as limiting the sample types applicable to the present invention.

As used herein, the term "tag" or "marker tag" refers to the small implantable marker that, when excited by an exciter's time varying magnetic field, will emit a "homing beacon" spectrum of frequency(ies) received by the witness coil(s) and used to determine its location. It may be programmed to produce a unique spectrum, thus permitting multiple tags to be implanted and located simultaneously.

Figure 3:
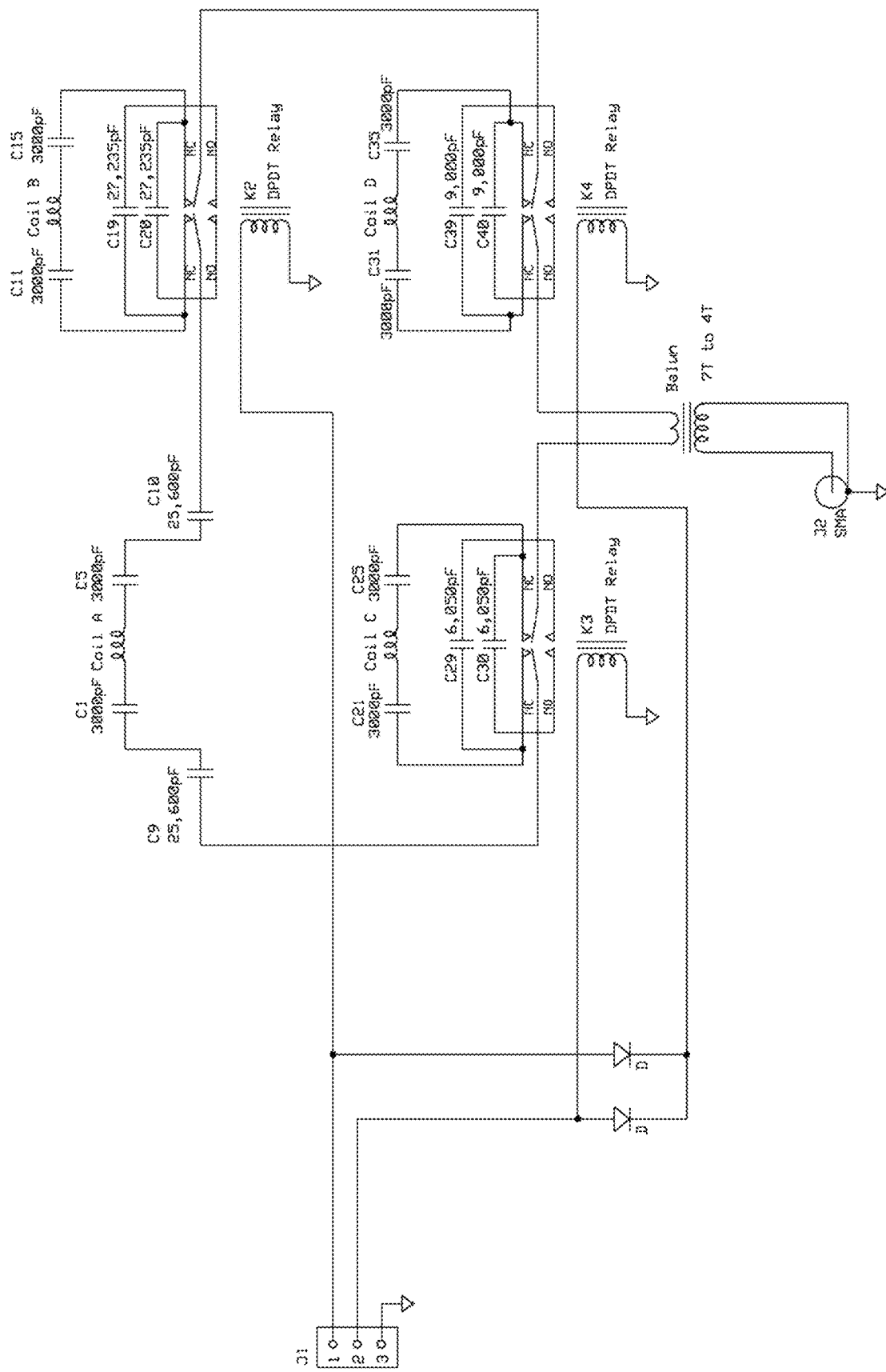

FIG. 3 shows an exemplary coil configuration of an exciter assembly.

FIG. 4A shows an exemplary exciter assembly 250 attached to controller 210 via a cable bundle 200.

Figure 4B:
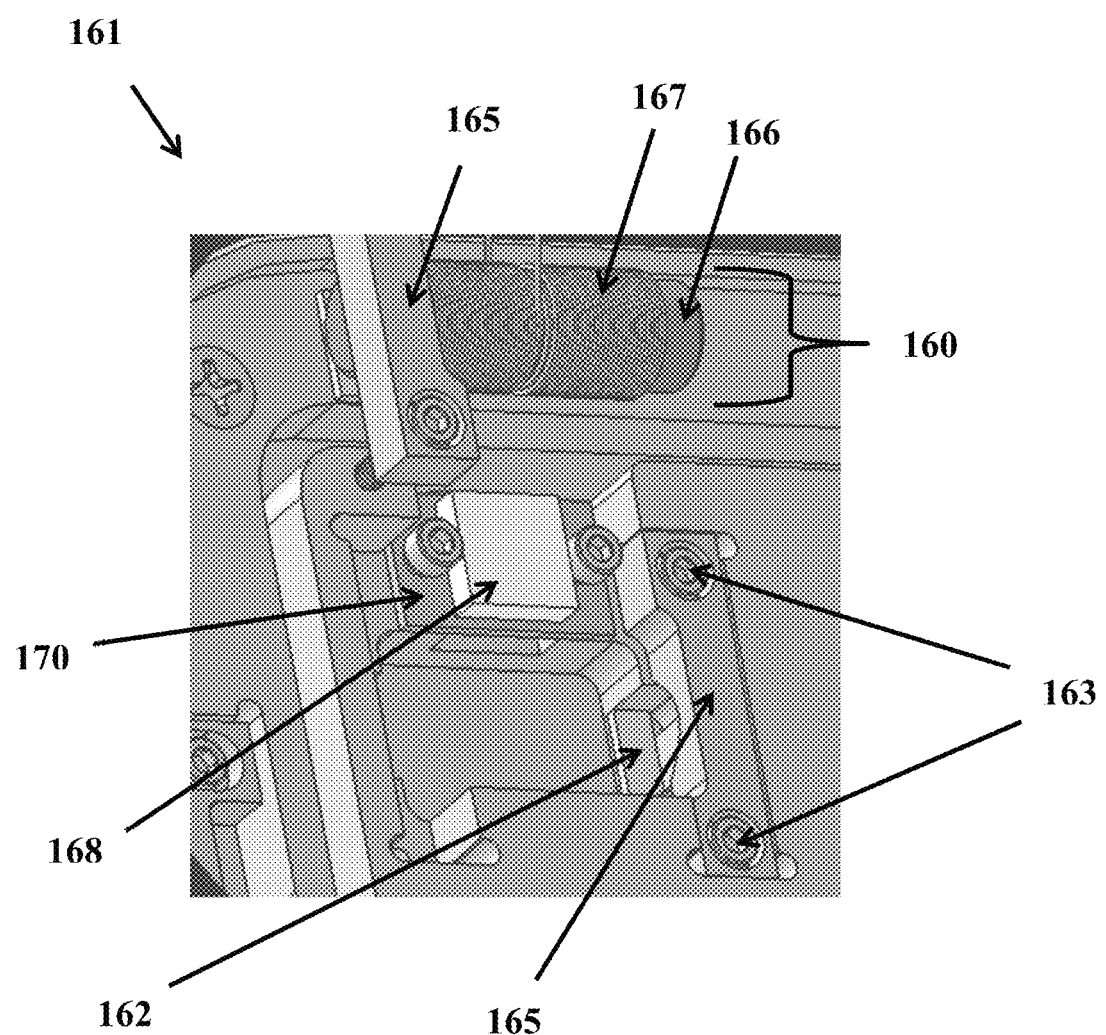

FIG. 4B shows an exemplary witness coil assembly (aka witness station assembly) 161.

Figure 4C:
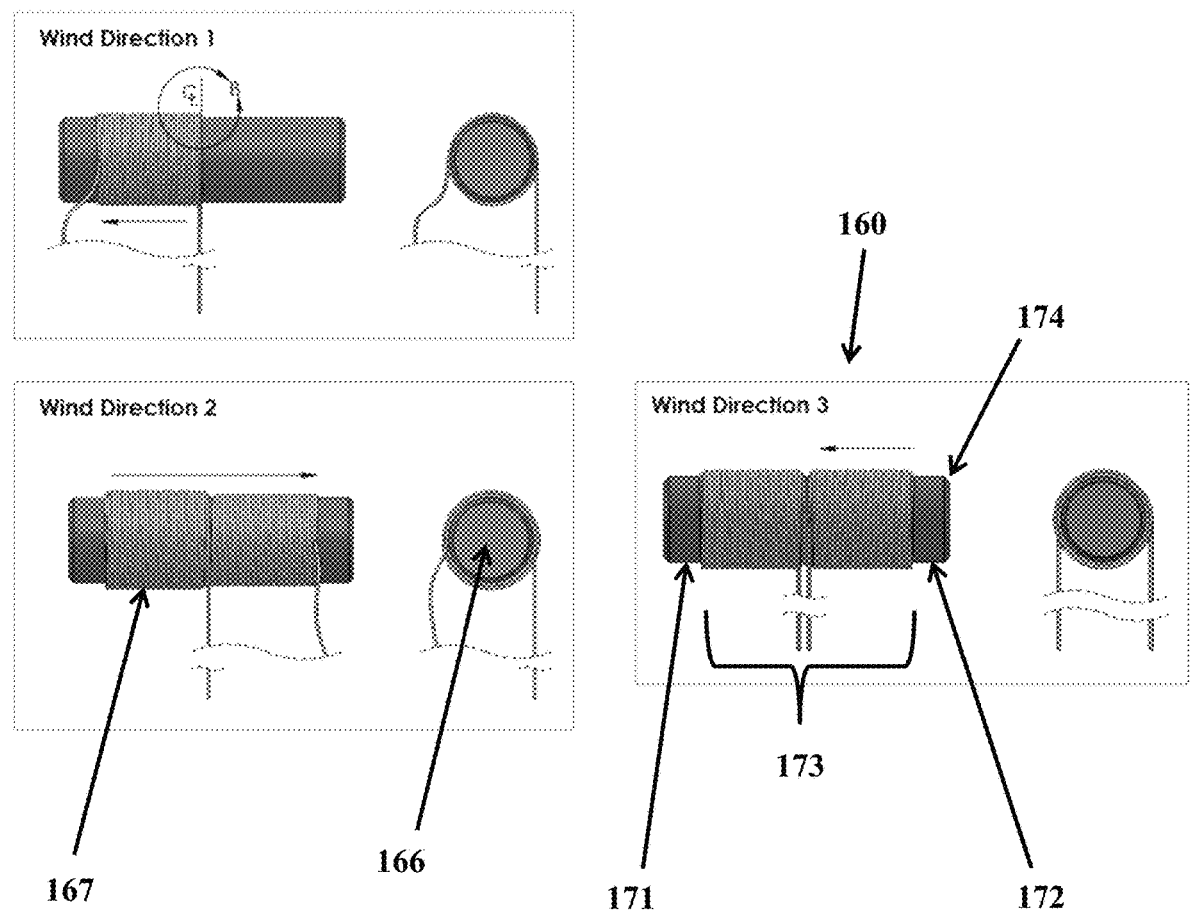

FIG. 4C shows an exemplary witness coil 160, including the three directions in which wire is wound to form coils 167 over the metal core 166.

Figure 5:
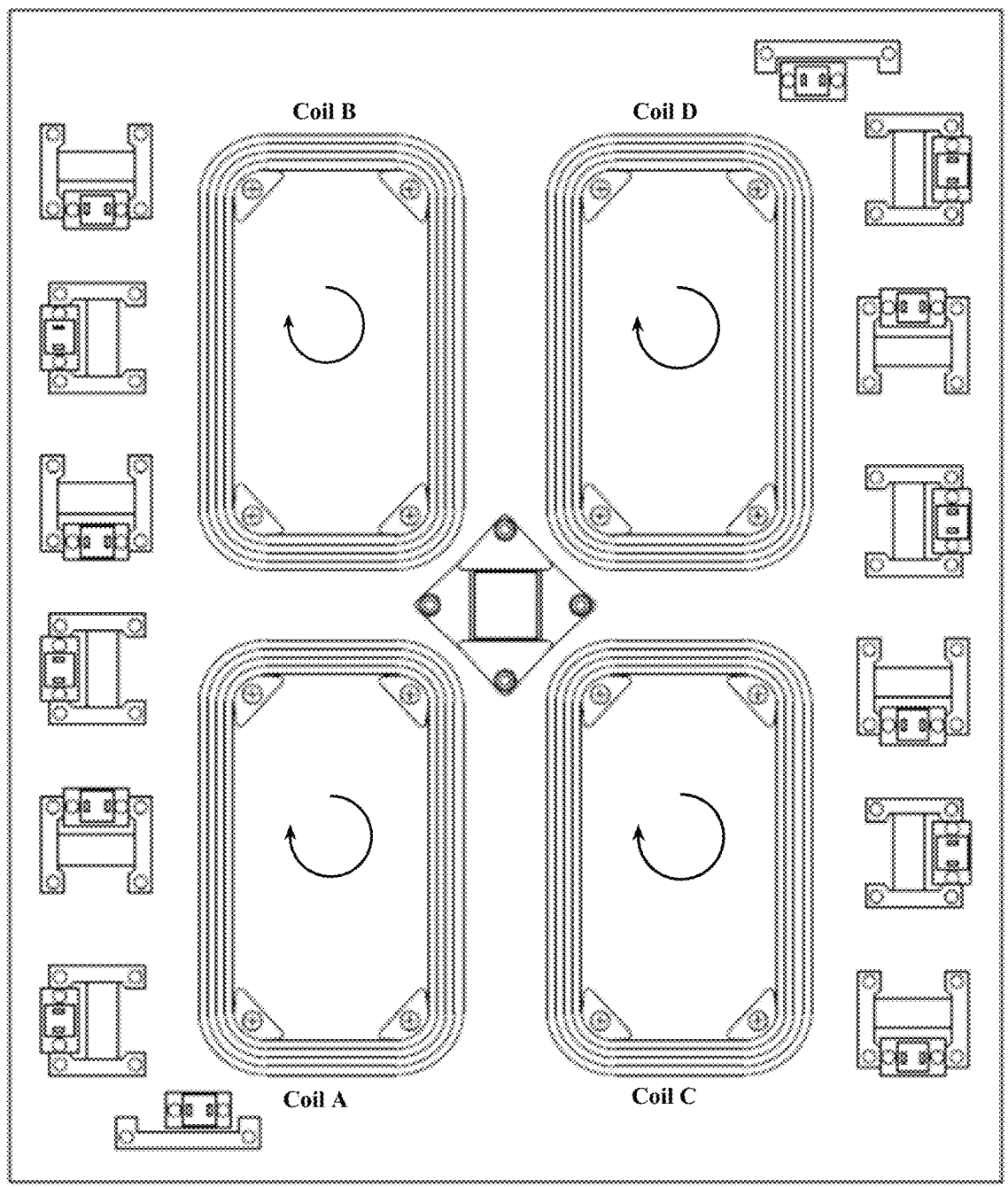

FIG. 5 shows an exemplary exciter assembly with four exciter coils (Coils A-D), where the current is flowing in the clockwise direction in all four exciter coils.

Figure 6:
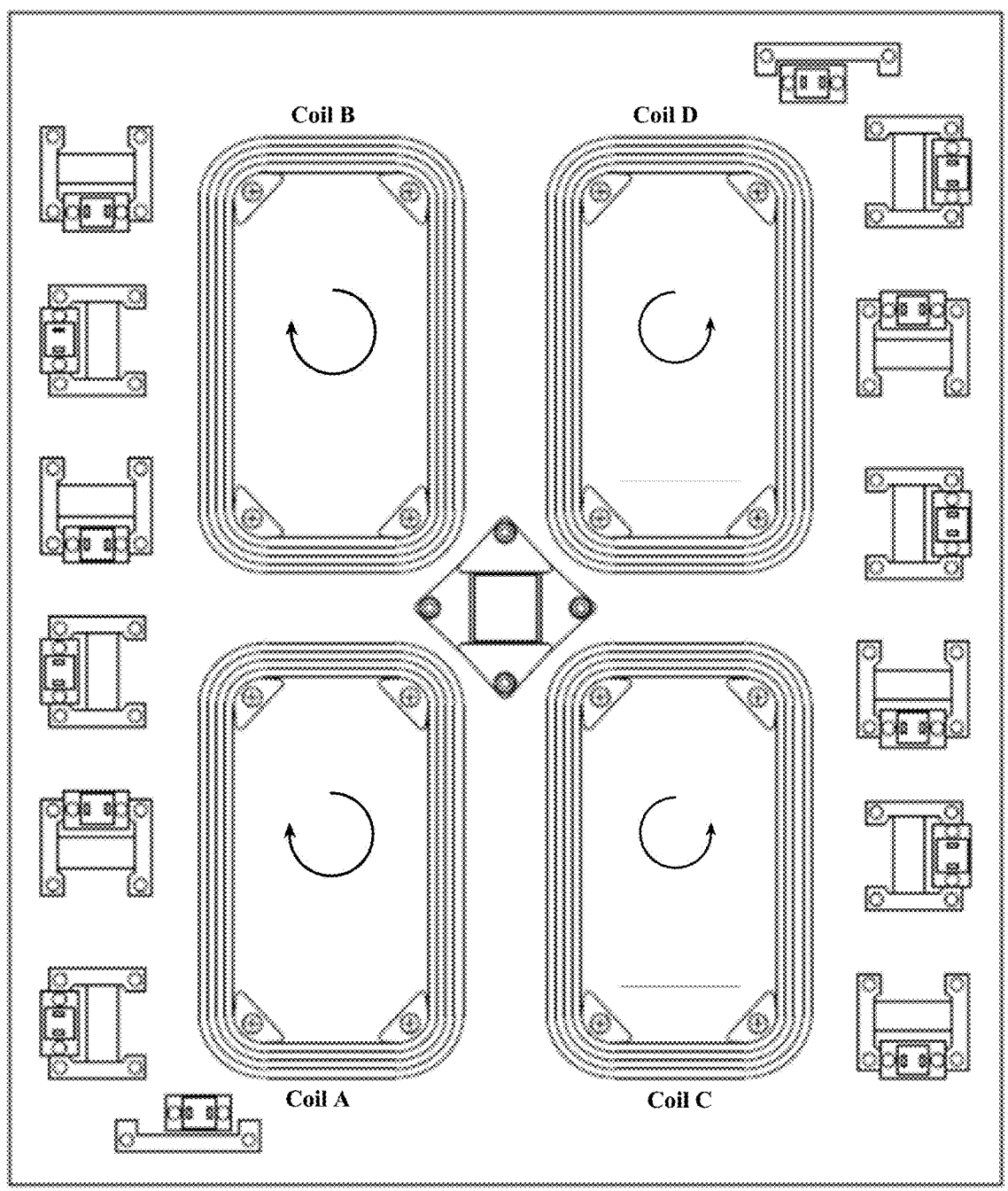

FIG. 6 shows an exemplary exciter assembly with four exciter coils (Coils A-D), where the current is flowing in the clockwise direction in Coils A and B, and flowing in the counterclockwise direction in Coils C and D.

Figure 7:
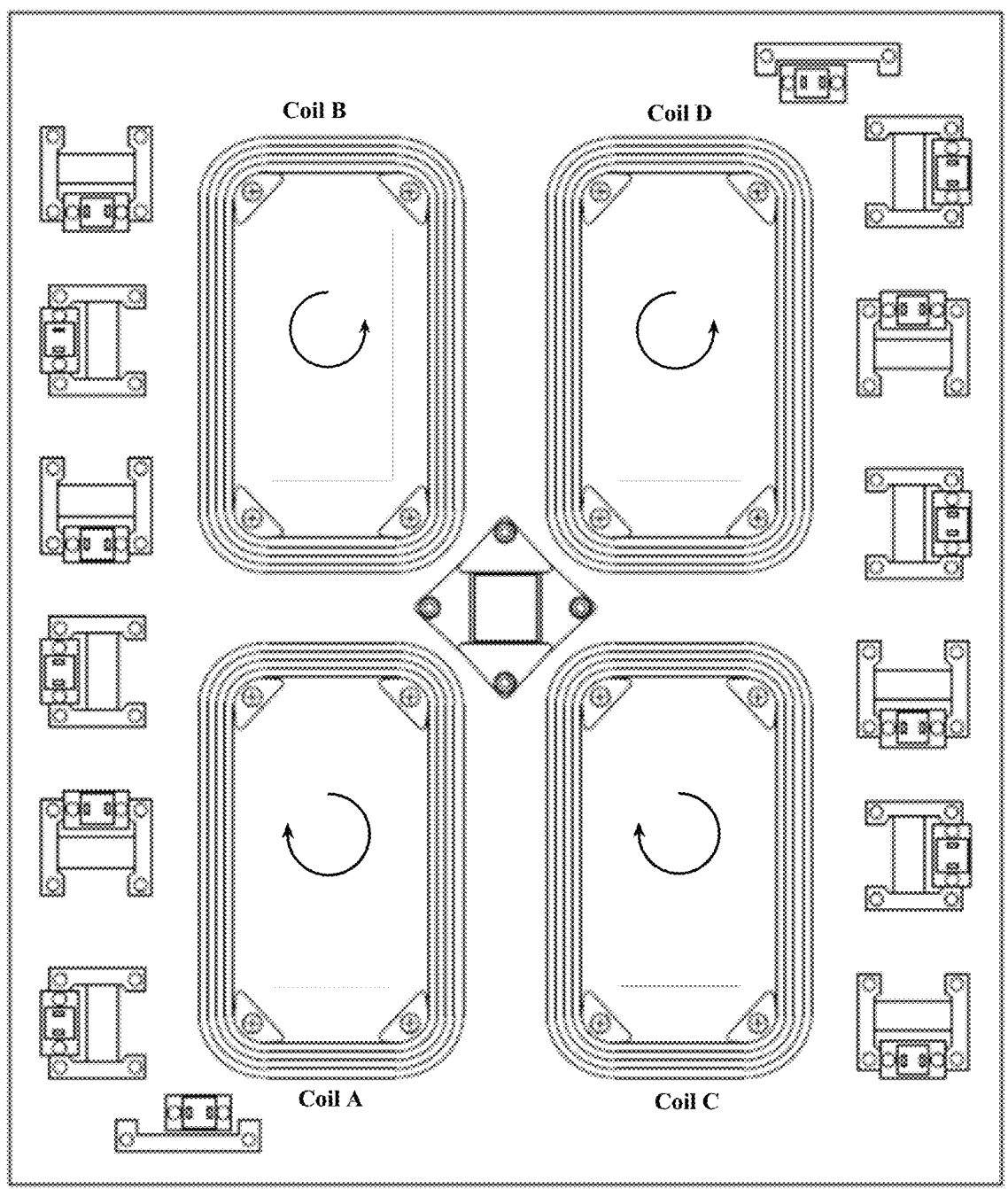

FIG. 7 shows an exemplary exciter assembly with four exciter coils (Coils A-D), where the current is flowing in the clockwise direction in Coils A and C, and flowing in the counterclockwise direction in Coils B and D.

Figure 8:
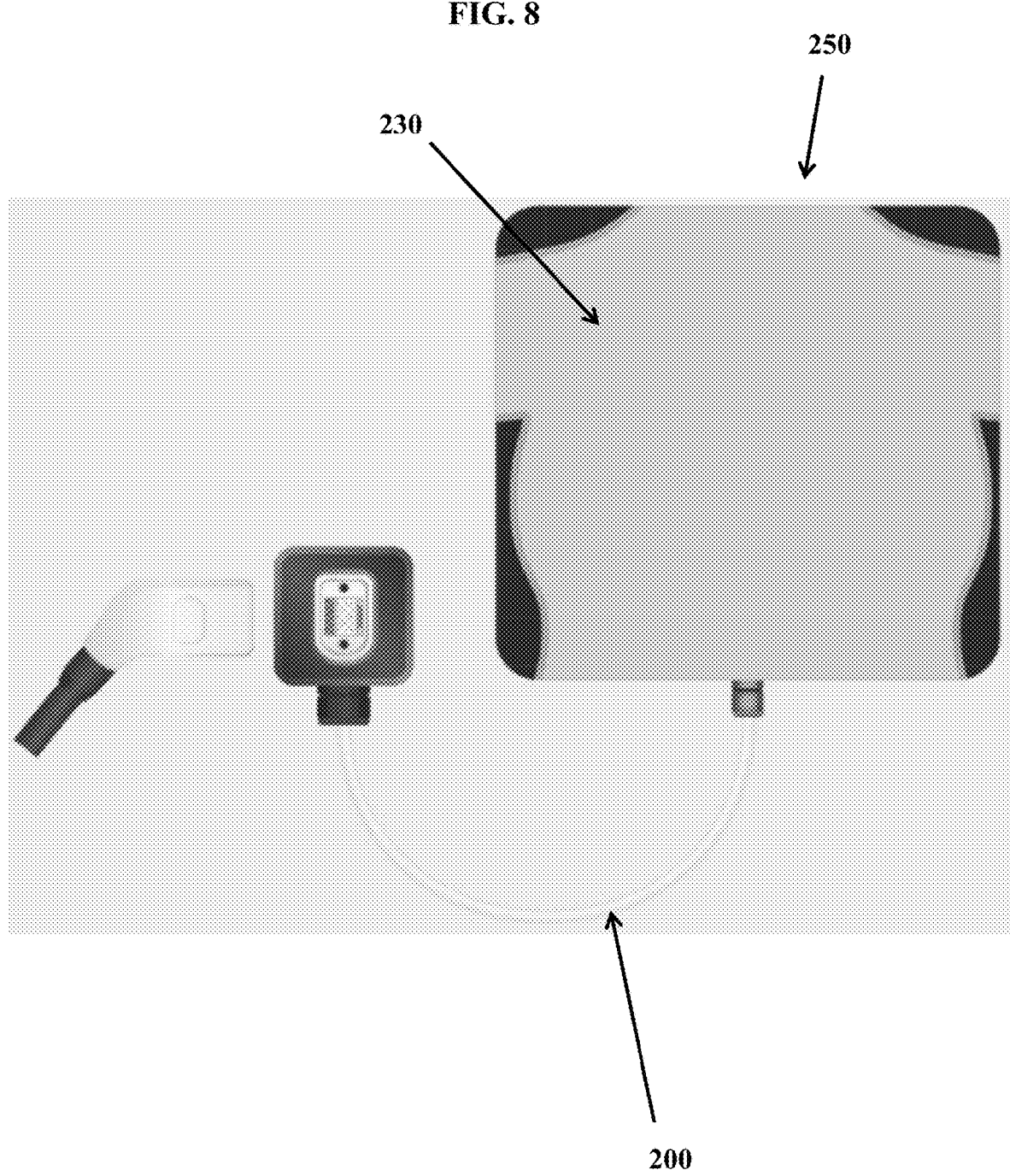

FIG. 8 shows an exemplary exciter assembly 250 with the top cover 230 on. The exciter assembly 250 is shown with cable bundle 200 leading therein.

Figure 9:
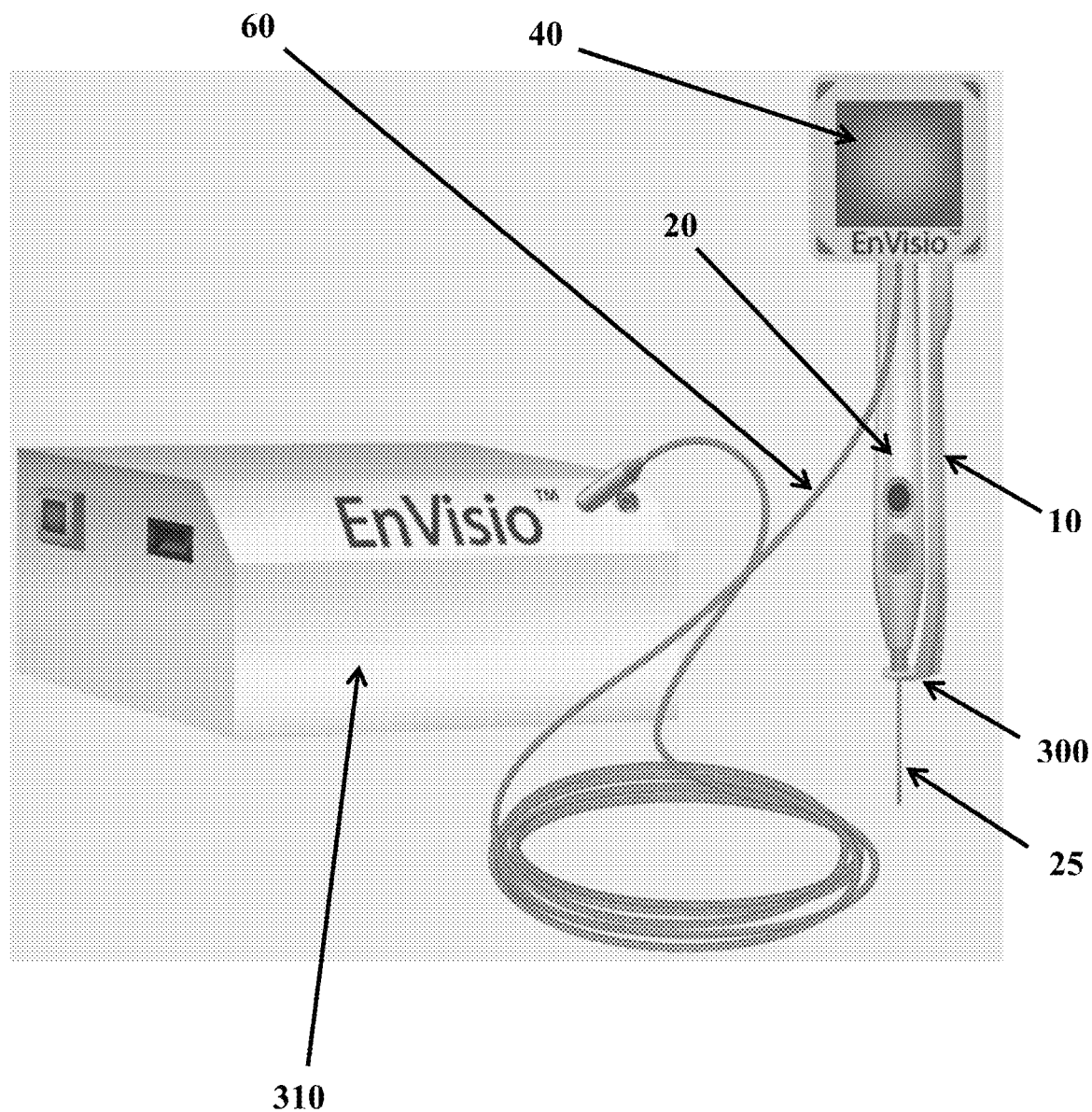

FIG. 9 shows an exemplary attachment component 10, with an angled distal end 300 that the distal tip 25 of the medical device 20 is inserted through.

Figure 10:
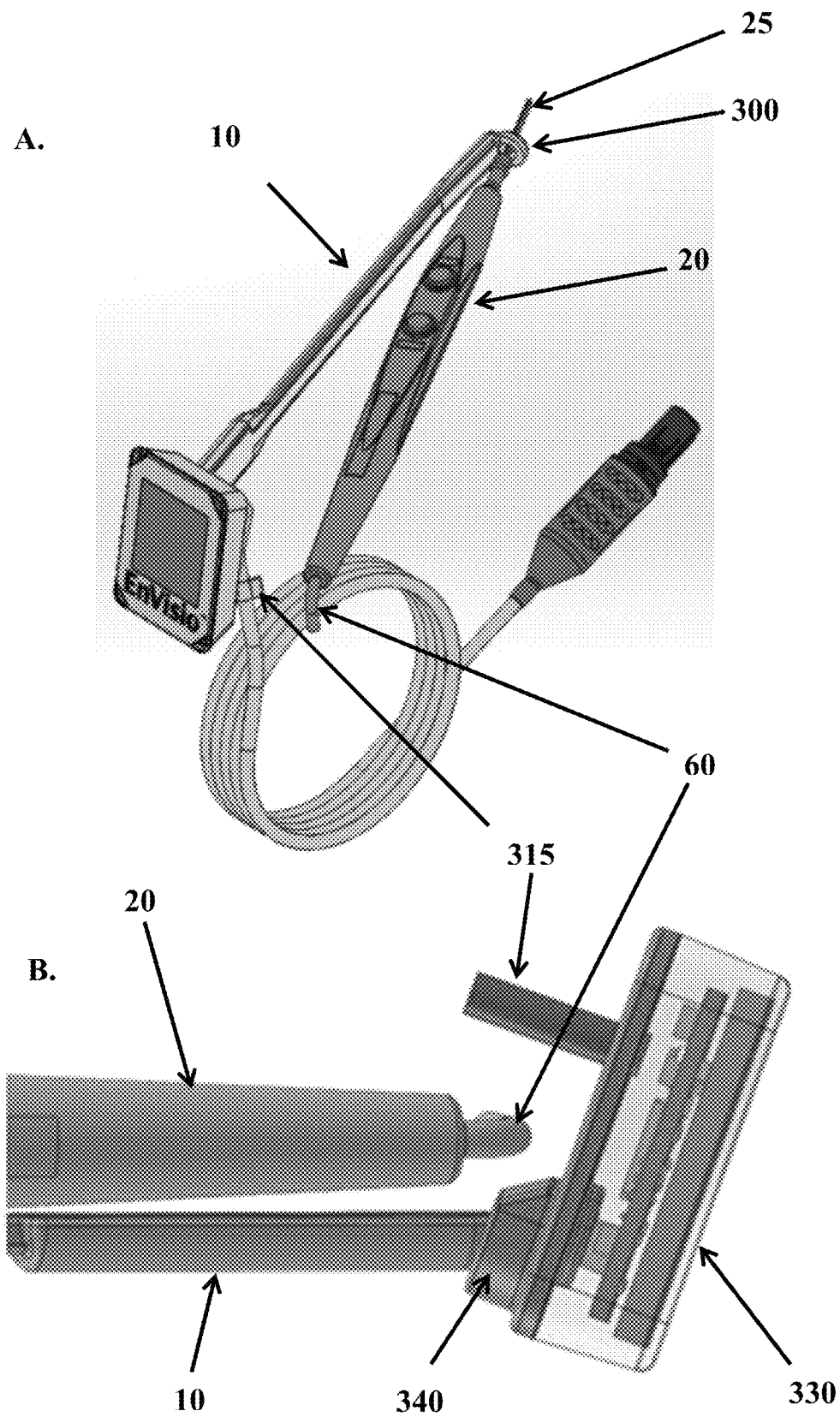

FIG. 10. Panel A shows the distal end 25 of a medical device 20 after it is initially inserted through the angled distal end 300 of attachment component 10. Panel B shows attachment component wire 60 prior to being attached to the cable management component 315 of the display component housing 330. Panel B shows attachment component wire 60 prior to being attached to the cable management component 315 of the display component housing 330. Panel B also shows the housing tapered connection 340 that the proximal end tapered connection 350 of the attachment component 10 is inserted into. The cable management component 315 has two clips that attached to and align both the attachment component wire 60 and the medical device wire 50.

Figure 11:
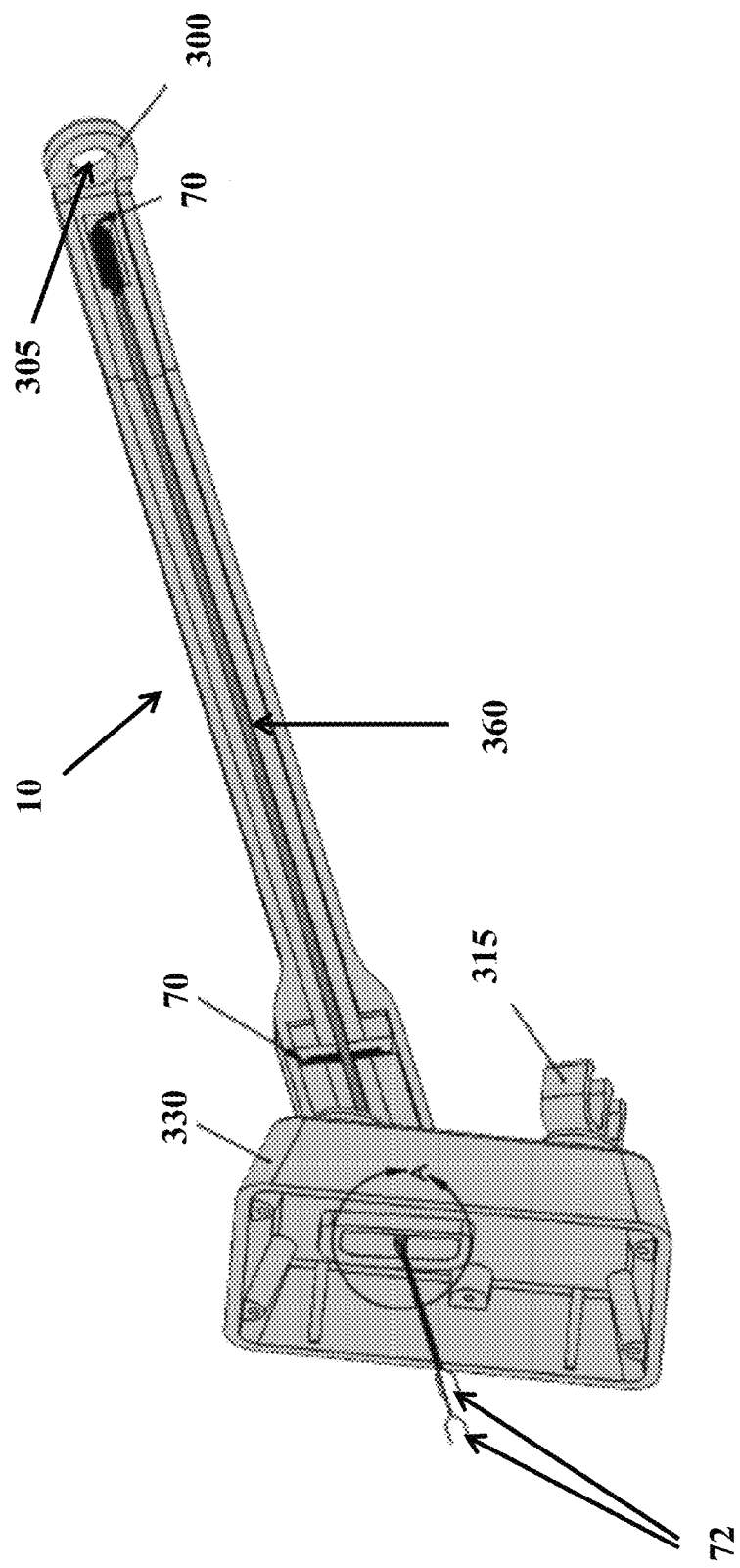

FIG. 11 shows an exemplary attachment component 10 attached to a display component housing 330. The attachment component 10 has a pair of location emitters 70, which are linked to location emitter wires leads 72 which are inside tube 360. The attachment component also has an angled distal end 300 with a distal end opening 305, which allows the tip of a surgical or other device to be inserted therethrough. The display component housing 330 has a cable management component 315, composed of a pair of clips for holding insulated wires.

Figure 12:
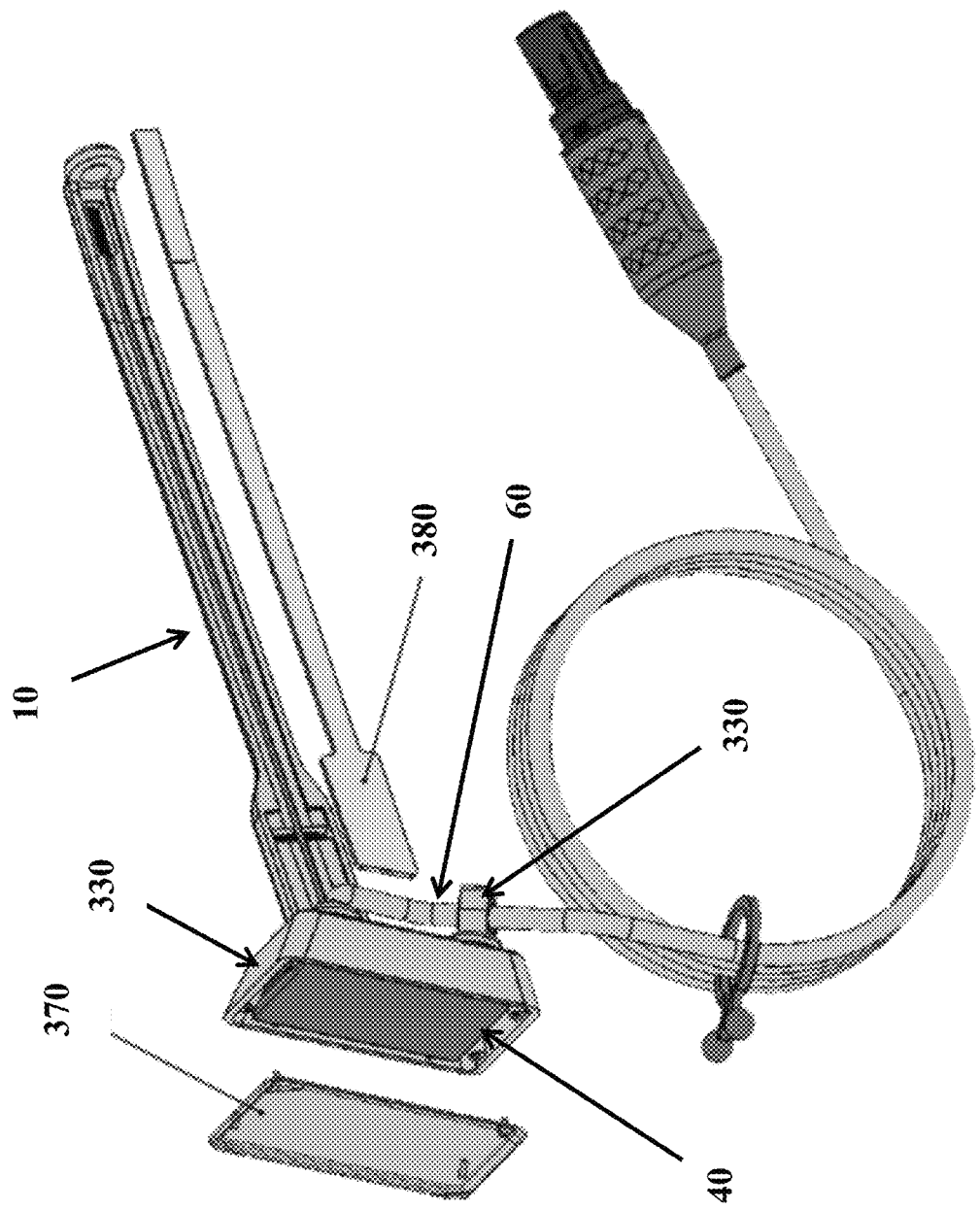

FIG. 12 shows an exemplary attachment component 10 attached to a display component housing 330 with a display component 40 located therein. A display cover 370 is shown, which is used to secure the display component 40 inside the display component housing 330. Also shown is an adhesive strip 380, which is shaped and sized to fit inside the attachment component and help secure a medical device to the attachment component.

Figure 13:
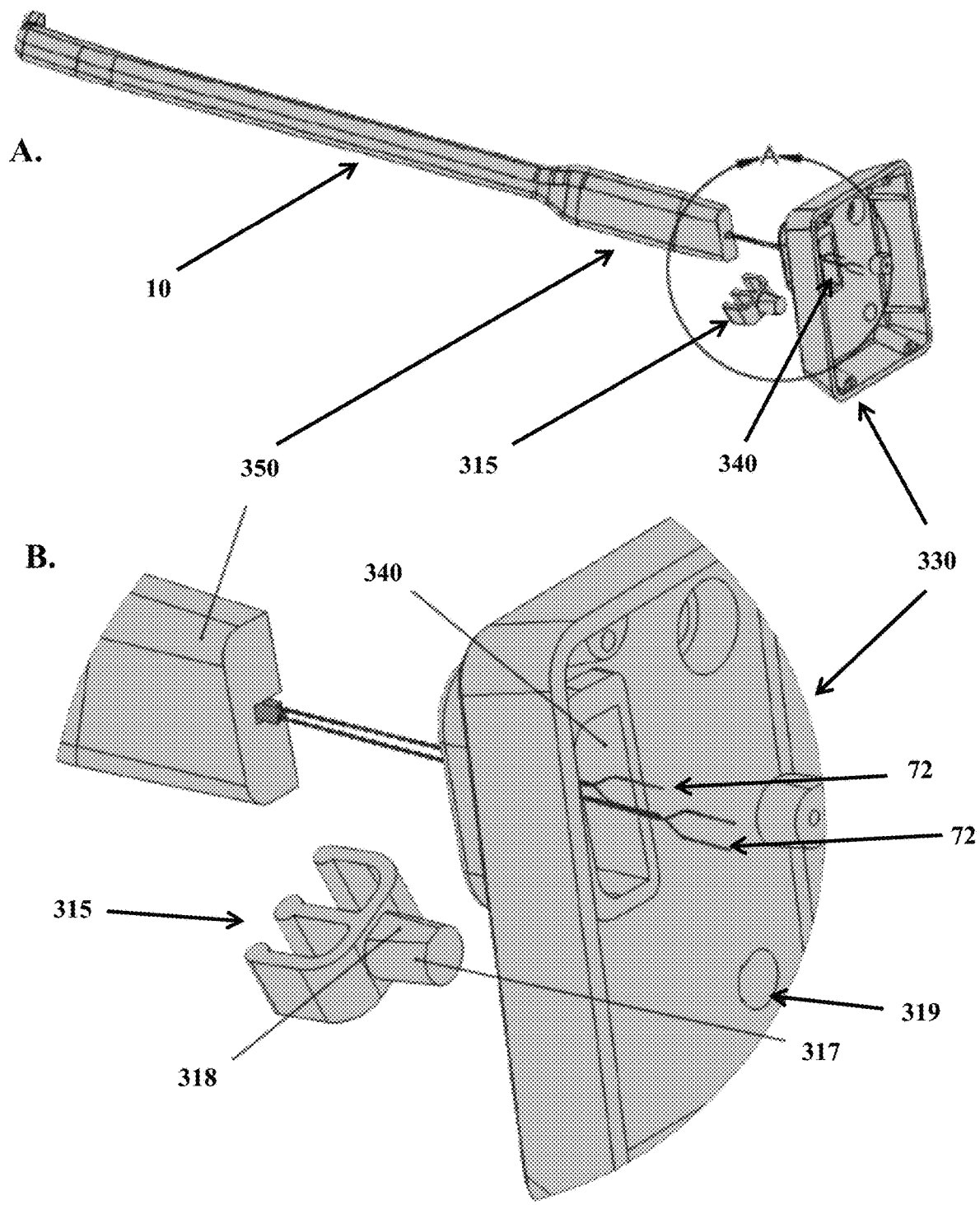

FIG. 13. Panel A shows the proximal end tapered connection 350 of the attachment component 10, which is configured to push-fit into housing tapered connection 340 of the display component housing 330. Panel B shows a close up of section A of Panel A, including cable management tapered connection 317 that is part of cable management component 315 and designed to be inserted into tapered connection hole 319 of display component housing 330. Cable management tapered connection 317 includes a flat part 318 to lock angular position.

Figure 14:
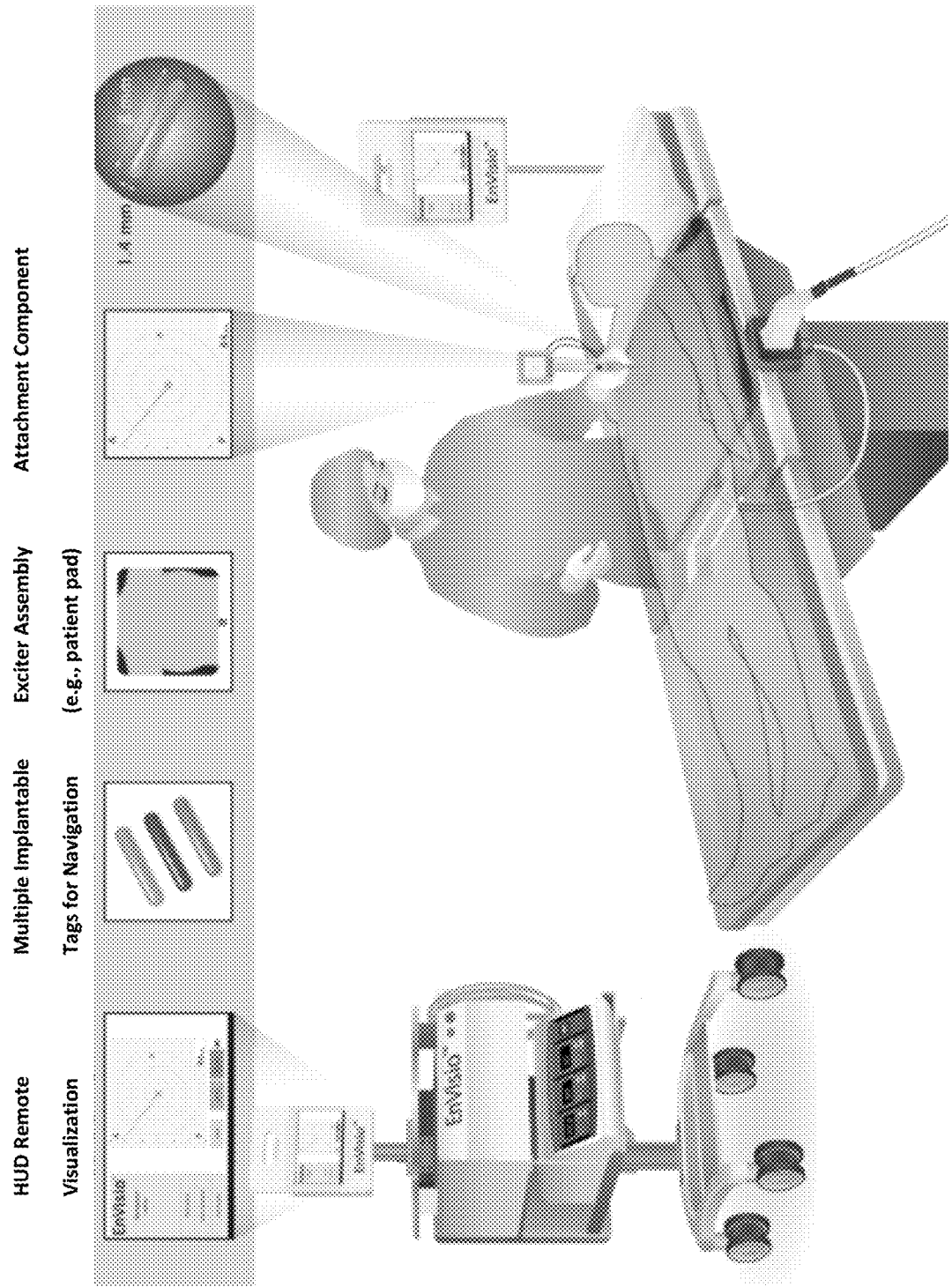

FIG. 14 shows an exemplary system for localizing a tag that is implanted in a patient. The system is composed of an exciter assembly that emits signals that activate the tag(s) in the patient. A systems electronics enclosure is shown as a mobile cart, which delivers signals to the exciter assembly and receives and processes signals from the tag(s) in the patient. Guidance for a surgeon is displayed on the display component, as well as on a screen on the systems electronics enclosure.

DETAILED DESCRIPTION

Provided herein are systems, devices, assemblies, and methods for generating exciter signals, for example, to activate a remotely located tag. The systems, devices, assemblies, and methods find use in a variety of application including medical applications for the locating of a tag in a subject. While the specification focuses on medical uses in human tissues, it should be understood that the systems and methods find broader use, including non-human uses (e.g., use with non-human animals such as livestock, companion animals, wild animals, or any veterinary settings). For example, the system may be used in environmental settings, agricultural settings, industrial settings, or the like.

A. Addressing Variable Alignment of an External Coil (e.g., Tag Coil) with the Exciter Assembly In some embodiments, the exciter is configured to provide power to a tag, independent of the alignment of the coil of the tag with the exciter. For example, in some embodiments, power transfer to a tag may be dependent on the relative orientation of the exciter magnetic field to the tag. In some such embodiments, absent a corrective measure, the tag may only collect power from the portion of field aligned to the tag's coil (e.g., a ferrite-core coil contained in the tag). This issue could be resolved by including multiple exciters capable of producing all three orthogonal directions of the magnetic field. This, however, leads to a thicker assembly and prevents both rejection of primary exciter coil (e.g., located in the exciter assembly) to sensing coil coupling (also located in the exciter assembly) (see section B below) and rejection of secondary field coupling between the tags/emitters and exciter coil that subsequently couple to the sensing coils and impair localization of the tags or emitters (see section C below). To address this challenge, provided herein are configurations of the exciter assembly that provide a mechanism of changing the orientation of the magnetic field with exciter coils that can be deployed in only one magnetic direction.

In some embodiments, this is accomplished by having multiple coils in the exciter assembly (see, e.g., FIG. 4A), and setting the direction of current within each coil to either clockwise or counterclockwise (see, e.g., FIGS. 5-7). In some embodiments, the coils are connected in series so that the same current is running in each. In some embodiments, a coil layout comprises four coils in two rows, centered at (X1, Y1), (X1, Y2), (X2, Y1), and (X2, Y2) coordinates with three sets of current flow configurations: Configuration 1: all current clockwise to simulate an exciter coil aligned with its plane normal to the Z axis; Configuration 2: coils centered at (X2, Y1), (X2, Y2) running current counter-clockwise to simulate an exciter coil aligned to the X axis; and Configuration 3: coils centered at (X1, Y2), (X2, Y2) running current counter-clockwise to simulate an exciter coil aligned to the Y axis. Any number of other coil configurations may be employed. For efficiency, it is desired (although not required) to minimize the number of components and overall complexity of the design. However, in some embodiments, it may be desirable to have more than four coils (e.g., 6, 8, 10, 16, etc.) in the exciter assembly to provide more flexibility for changing field directionality, albeit at the expense of system complexity.

Tuning of the coils in the exciter assembly for each configuration requires less change between configurations when the same current is flowing through all the coils in every configuration. This is because the effect of one exciter coil on the others is dependent on the state of the first exciter coil (open circuit, current-carrying, etc.).

To provide optimal performance, the area of the exciter coils should be maximized, and the distance between the centers of the coils should be maximized. A larger area coil provides a higher field for the same applied current. Coils separated by larger distances provide a larger directional change for Configurations 2 and 3.

FIG. 3 provides an exemplary schematic of a four coil exciter assembly in some embodiments of the invention, with the four coils labeled Coil A, Coil B, Coil C, and Coil D (see FIG. 4A).

For medical uses, where the exciter assembly is provided in a flat planar mode (e.g., pad) beneath a patient, a clinically preferred system geometry entails that all four coils are placed very close to each other. As a result, the magnetic coupling between each coil varies with individual coil polarity and therefore the total inductance of all four coils in series varies with coil polarity combinations. Thus, optimal performance will necessarily balance competing factors. To compensate for this, in some embodiments, a system of switching is employed in which additional series capacitive reactance is inserted when the total inductance is increased so that the tuning center frequency is maintained at the desired excitation frequency. In a preferred embodiment shown in FIG. 3, relays are utilized for switching. Other embodiments may employ solid state switching approaches such as PIN diodes. Any suitable mechanism that achieves the switching may be employed.

In some embodiments, the centers of the coils are separated by 10 ... 50 ... 100 ... 500 ... or 1000 cm. In some embodiments, each coil is from 25 ... 625 ... 2500 ... 62,500 ... or 250,000 $cm^2$ in area. The largest total series capacitance is needed for a condition when all four coils have the same polarity. In some embodiments, this series capacitance is distributed equally among all four coils, balanced on each side of the switching relay as shown in FIG. 3. Distributing capacitance this way keeps the contact voltage present at the switch to a minimum. Otherwise, the high "Q" of the coils could result in excessively high voltage, exceeding 10 KV for some configurations, present at the switches and interconnects.

Additional capacitance useful for maintaining a desired resonant frequency as described above (e.g., adding capacitors in series to reduce the capacitance) is switched in by the polarity switching relay or a separate switch that may be energized when needed. In some embodiments, this capacitance is distributed among the polarity switching relays to both minimize terminal voltage and minimize common mode coupling by achieving best symmetry.

In some embodiments, each capacitance element is comprised of multiple capacitors to minimize the voltage across each capacitor to ensure the voltage capability of the capacitors is not exceeded and to minimize heating due to losses that might otherwise cause the resonant frequency to drift.

In some embodiments, a balun is incorporated as close as possible to the exciter coils (see Section D below and FIG. 3). The balun described below accomplishes common mode rejection to reduce or eliminate electric field generation and also provides an impedance transformation to optimally match the coil assembly impedance to that of the transmission line and power amplifier. In a some embodiments, the primary (amplifier side) of the balun has 8 turns and the secondary (coil side) has 4 turns, thus providing a 4 to 1 change in impedance that nicely matches, for example, a 50-ohm generator output impedance to a 12-ohm coil impedance at resonance. Other turns ratio may be employed for optimal impedance transformation to other characteristic impedance transmission lines and amplifiers.

FIG. 3 provides an exemplary embodiments of the coil system employed in the exciter assembly. In this figure, a plurality of capacitors are identified by number (e.g., C1, C5, C11, C40 etc.; pF (picofarads)) and their relative position to Coils A, B, C, and D (see, e.g., FIG. 4A). A balun with a 7:4 turn ratio is shown (Balun transformer ratio matches impedance to 50 Ohms, employing 7:4 ratio, with 7 turns on the 50 ohm side and 4 turns on the coil side). The system may be configured or adjusted to optimize performance based on the manner in which the coils are utilized. For example, as shown in the exemplary embodiment in FIG. 3:

Field: Z-plane (++++) capacitors C9 and C10 are 25,600 pF (20,000 in parallel with 5,600 pF);

Field: X-plane (+−+−) capacitors C19 and C20 are 27,235 pF (used 27,000 pF in parallel with series combination of (2) 470 pF capacitors);

Field: Y-plane (++−−) capacitors C29 and C30 are 6,050 pF (2,700 parallel with 3,300 pF in parallel with series combination of (2) 100 pF capacitors);

Common (all fields): capacitors C39 and C40 are 9,000 pF (parallel combination of (3) 3,000 pF capacitor); and C39 and C40 capacitors (value XY-fixed) are 9,000 pF (18,000 pF in series with 18,000 pF; could be 9,220 pF; 8,200 in parallel with 820 pF or other combinations; total voltage is 660 Vrms).

Other specific values of capacitance may be utilized to provide the desired resonance frequency or frequencies with different values of inductance that may result from different coil constructions.

B. Addressing Exciter Field Strength Near Sensors

The exciter field strength used to power the tags, in general, is close to the exciter in order to create a large volume in which a tag or tags can be powered. This field is much larger than the field provided by the tag or tags or the emitters associated with a surgical tool (the tags and emitters collectively and individually referred to herein as "the beacons"). Also, since a single excitation assembly device is preferred to both provide excitation and sensing, the sensing components should be in close proximity to the exciter components. Therefore, the magnetic field sensors would normally sense a magnetic field at the exciter frequency that is very large, on the order of 160 dB or more larger than the signals of interest (from the beacons).

This issue can be partially resolved by means of electronic filters. However, the rejection capabilities of these filters are limited, they are expensive, and they are physically large. Filters may be active or passive. However, active electronic filters have an inherent noise floor that limits dynamic range and filtering effectiveness for this very high dynamic range situation so passive filters may be employed in some embodiments.

An alternative (or additive) solution takes advantage of the coil system described in Section A above. In such embodiments, one can reduce the exciter field pickup by the sensors by taking advantage of the vector nature of the magnetic field. In some embodiments, an exciter coil with an orientation generating only magnetic flux substantially perpendicular to the X-Y plane containing the sensing coils is selected. In some embodiments, ferrite-core coils, which are also highly directional in nature, are then aligned to that plane, such that magnetic flux orthogonal to the plane is not sensed. This produces rejection of the exciter field by more than 40 dB. In a preferred geometry, greater than 70 dB of isolation has been achieved for all sensing coils in all three polarity configurations described above. Both the height and tilt of each witness coil is adjusted to achieve the alignment needed to achieve this level of isolation for all three coil polarity conditions. Isolation is typically measured using a Vector Network Analyzer by connecting the exciter coil to port 1 and a specific witness coil to port 2. The magnitude and phase of $S_{21}$ is then measured at the receive frequency. In a preferred embodiment, the receive frequency chosen is 130.2 KHz.

In such embodiments, the system therefore uses one magnetic field direction for excitation, and the two remaining directions (orthogonal to the excitation direction) for sensing. In other embodiments, one can use two orthogonalities for excitation and one orthogonality for sensing. However, it may be preferable to use two orthogonalities for sensing to provide faster estimates of the beacon position(s).

C) Addressing Exciter/Beacon Coupling

In some embodiments, the exciter is a highly resonant coil. Because, in some embodiments, the beacon's frequency is close to the resonant frequency of the exciter, a portion of the beacon's AC magnetic field aligned to the exciter coil orientation may induce current flow in the exciter and therefore produce a magnetic field in the exciter coil orientation at the beacon frequency. This effect distorts the original field from the beacon, making it more difficult to localize the beacon. In a clinically preferred geometry, this distortion masks the true location of the beacon such that navigation may become difficult or impossible.

This coupling can be diminished by choosing a different beacon frequency less close to the exciter resonance. However, because, in some preferred embodiments, the beacons utilize a single ferrite core RF coil for both reception and transmission, the available bandwidth is limited.

Using the exciter configuration described in Sections A and B above, instead, since the sensing system comprised of sensing coils is oriented orthogonal to the exciter coil, the distorted field is not sensed. In other words, distortion is limited to the magnetic field direction that is substantially aligned to the exciter coil, which is orthogonal to the sensing system. The true location of the beacon is thus no longer masked by the field distortion produced by the exciter current flow at the beacon frequency so accurate navigation is achievable without artifact.

D) Addressing Electric Field Magnitude Produced by the System

The exciter and associated circuitry should be designed to minimize the electric field magnitude produced by the system. If produced, electric fields can couple capacitively into the sensing system and degrade system accuracy. Electric fields also interact with the patient and the environment much more significantly than magnetic fields.

In some embodiments, this challenge is addressed by incorporating a balun as close as possible to the exciter coils. The balun, which can also act as an impedance transformer, minimizes electric field by eliminating asymmetric current flow with respect to ground. Another way to think of this is that the balun eliminates common mode coupling. In some embodiments, on the exciter side of the balun, the circuit design and layout should be as symmetric as possible to maintain balance.

In addition to reducing electric field effects, the transformer allows off the shelf 50-ohm coaxial transmission line to be used without mismatch. This scales transmission line voltage and current to optimally transmit power to the exciter assembly with the best efficiency and the smallest, most flexible, coaxial cable.

E) Identifying and Managing Locations of Multiple Beacons

In some embodiments, one or more beacons (e.g., tags, emitters associated with one or more surgical devices, or other objects whose location, position, relative position, or other spatial information desired) are employed. In some embodiments, each different beacon generates a unique frequency, spectrum of frequencies or otherwise distinguishable signal. In some such embodiments, a hunting algorithm is employed to identify the spatial information of one or more of the beacons. In some embodiments, the optimal exciter polarity and power level is identified for each beacon (e.g., accounting for any relative orientation of beacon to the exciter) by cycling the exciter through different planes. Based on this information, an optimal exciter pattern is calculated to maximize the quality of the procedure and accuracy of information conveyed to a user (e.g., treating physician). In some such embodiments, a first optimal pattern is utilized to provide spatial information about a first tag and a first portion of a procedure is conducted. Next, a second optimal pattern (which may be the same or different) is utilized to provide spatial information about a second tag and a second portion of a procedure is conducted. Further cycles may be conducted for additional tags. Alternatively, the exciter pattern (polarity and power) may cycle between multiple, different optimal patterns during a procedure to provide near real-time optimal spatial information of multiple beacons. In some such embodiments, rapid switching of coil polarity in the emitter is employed to simultaneously or near-simultaneously power two or more beacons.

F) General Description of Exemplary System and Device Components

In some embodiments, the systems, devices, assemblies, and methods find use in electromagnetic navigation systems that power a remote tag device with a sinusoidal magnetic field (see e.g., U.S. Pat. No. 9,730,764 and U.S. application Ser. Nos. 15/281,862 and 15/674,455, herein incorporated by reference in their entireties). In some embodiments, the tag is wireless and ideally minimally sized. In some embodiments, while powered, the tag generates its own time varying magnetic field at one or more sideband frequencies. The shape of the magnetic field is approximately that of a magnetic dipole positioned at the tag. By monitoring the magnetic field at several positions with receiving antenna coils, also called sensing or witness coils or witness stations, the location of the tag is identified. In some embodiments, the systems, devices, assemblies, and methods further comprise an electrosurgical tool. In some embodiments, the electrosurgical tool, or a component attached to or in physical proximity to the tool, comprises two or more location emitters that also generate a magnetic field similar to a magnetic dipole. In some embodiments, the emitters are driven with two different frequency signals that are also different from both the exciter frequency and the tag response frequencies. In certain embodiments, the location emitters are wired to a signal supply source.

Figure 1:
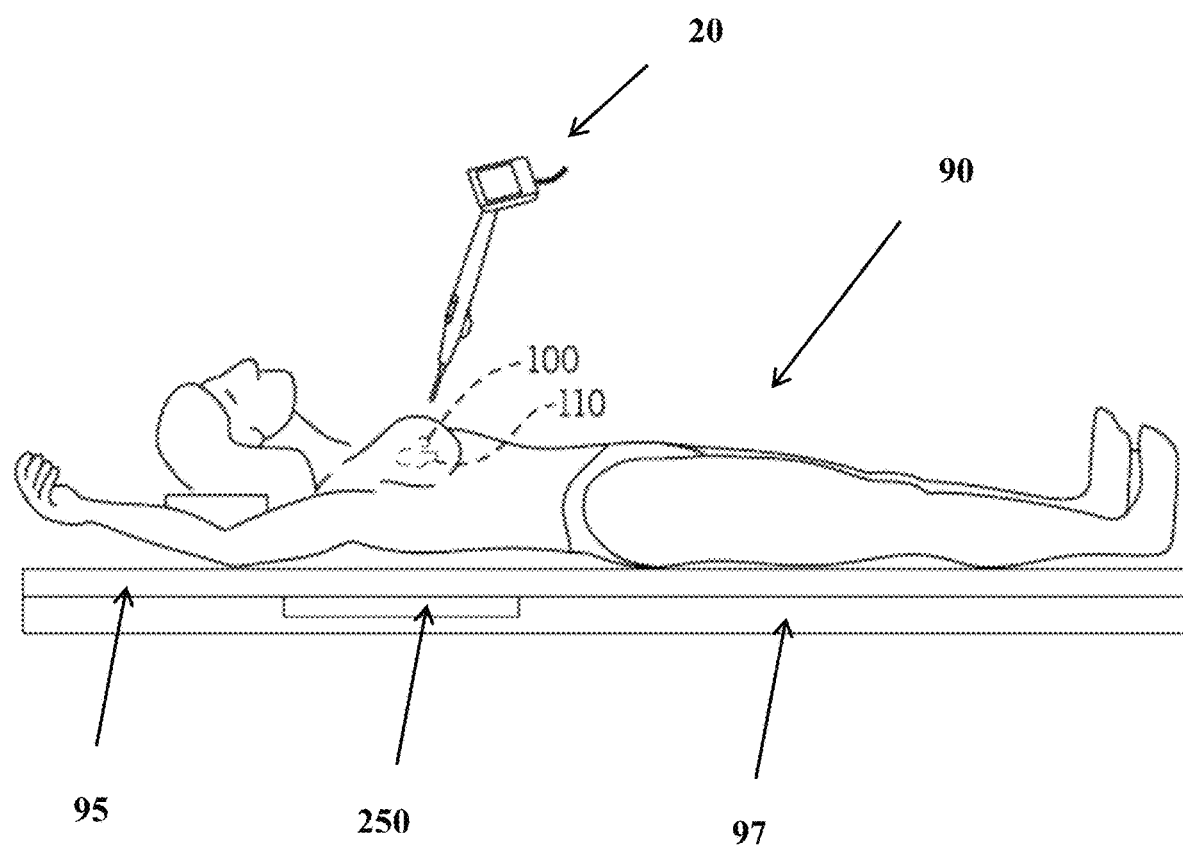
FIG. 1 shows an exemplary positioning of an exciter assembly, a medical device with display component attached, and a patient with a tag implanted next to a tumor.

In some embodiments, a single exciter assembly is employed (e.g., as shown in FIG. 4A) to generate signals that interact with the tag and the location emitters in the attachment component associated with the electrosurgical tool. In some embodiments, the exciter assembly is contained in a single thin assembly. In some embodiments, the assembly comprising the exciter further comprises sensors (e.g., the receiving antenna/sensing/witness station coils). In some embodiments, the exciter assembly is configured to be deployed under a patient that is undergoing a medical procedure. An exemplary procedure configuration is shown in FIG. 1 with patient 90 positioned on a surface 95 (e.g., mattress or operating table). The surface 95 is held by a surface frame 97. The patient 90 has a lesion (e.g., tumor) 110 and an implanted tag 100 positioned near, on, or in the tumor. An exciter assembly 250 is positioned beneath the patient, and beneath the surface (e.g., on the surface frame 97), and generates an electromagnetic field (not shown) in a region around the patient encompassing the position of the tag 100 and a medical device 20 (e.g., surgical device) in the operating field above the patient.

Figure 2:
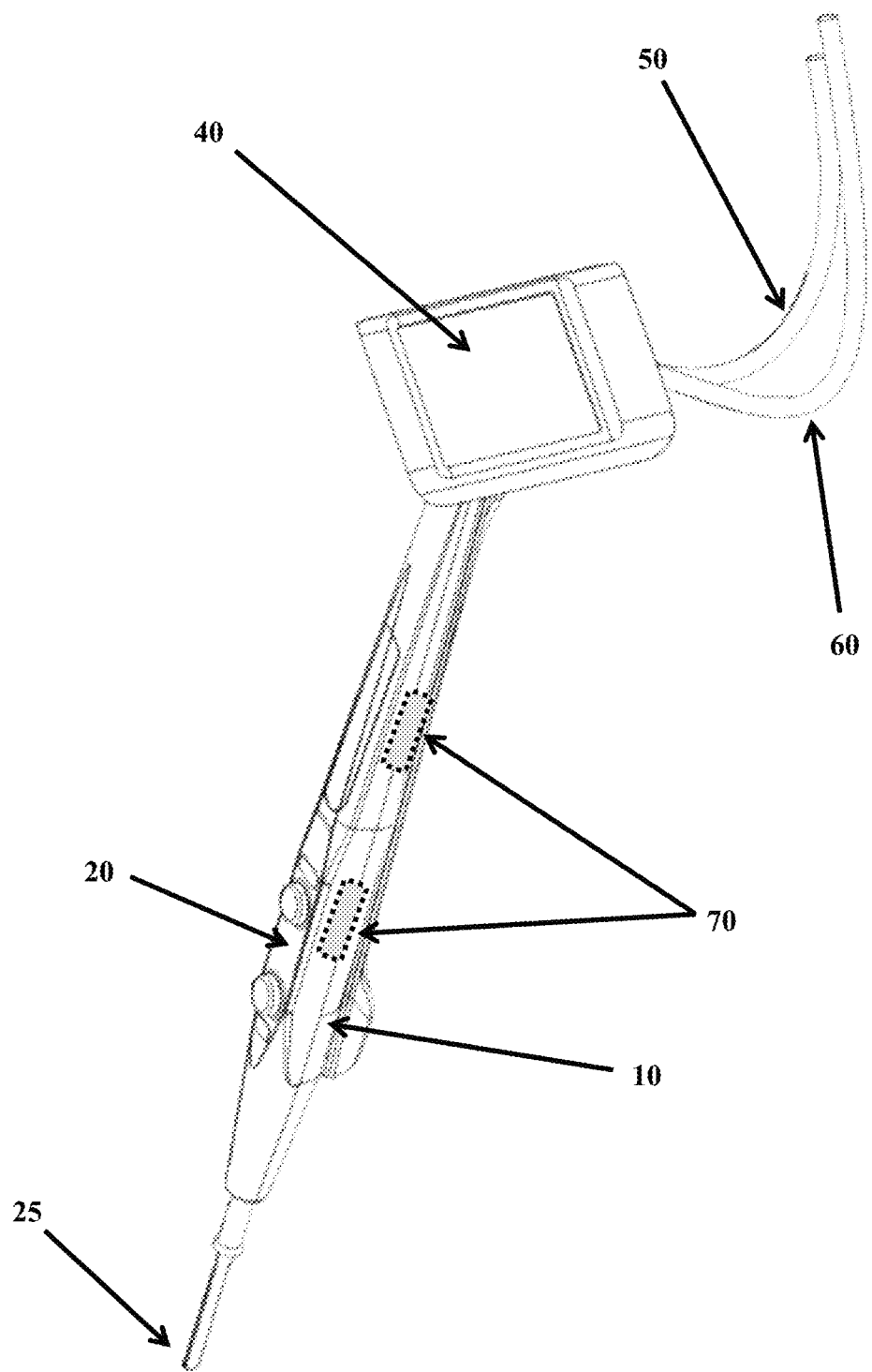
FIG. 2 shows an attachment component 10 that is attached to a medical device 20, which has a device tip 25. The attachment component 10 has two location emitters 70 located therein. The attachment component 10 is attached to, or integral, with a display component 40.

FIG. 2 shows an exemplary electrocautery surgical device (e.g., BOVIE) that finds use in some embodiments of the invention. The device 20 includes a tip 25 providing an operating surface for treatment of tissues, two embedded location emitters 70 allows the system to sense the location and position of the device 20, and a display unit 40 that provides visual information to a user (e.g., surgeon) about the location of a tag in the patient.

In some embodiments, the exciter assembly is configured to provide enhanced detection of remote objects (e.g., tags and surgical devices) under a number of different settings that would otherwise complicate location, position, and distance assessment, particularly real-time assessment of such factors.

In some embodiments, the systems and methods comprise a plurality of components. In some embodiments, a first component comprises one or more tags (which may be used interchangeably with the term "marker") whose location, position, distance, or other properties are to be assessed. In some embodiments, the tags are configured to be positioned in a subject at a surgical location or other clinically relevant location to mark a target region within a body. In some embodiments, a second component comprises a remote activating device (e.g., exciter assembly) that generates a magnetic field. In some embodiments, the second component is located in a device positioned near (e.g., below) a subject containing the one or more tags. In some embodiments, a third component comprises a plurality of witness stations configured to receive a signal generated by the one or more tags upon being exposed to the magnetic field generated by the second component. In some embodiments, the second and third components are physically contained in the same device (e.g., as shown in FIG. 4A). In some embodiments, a fourth component comprises a medical device location emitter. The fourth component can be integrated into a medical device or attached or otherwise associated with an attachment component (e.g., sheath). The fourth component comprises one or more location emitters (e.g., antennas that emit signals or other types of emitters) that generate signals via electrical wire feeds or upon exposure to the magnetic field generated by the second component, said signals detectable by the third component. In some embodiments, a fifth component comprises a computing device comprising a processor that receives information from the witness stations of the third component and generates information about the relative locations, distances, or other characteristics of the tags, the medical device, and the witness stations. In some embodiments, the fifth component comprises a display that displays such generated information to a user of the system.

In some embodiments, the first component is a single tag. In some embodiments, it is two or more tags (e.g., 3, 4, 5, 6, 7, 8, 9, 10, 11, 12, etc.). In some embodiments, where more than one tag is employed, the tags are of identical type while in other embodiments they are of different type.

In some embodiments, the tag comprises a ferrite-core coil antenna (e.g., resonant at 100-200 kHz) coupled to an integrated circuit (IC), which is powered by an AC magnetic field at resonance. In some embodiments, the core is contained in an enclosure (e.g., a cylindrical glass or plastic housing). In some embodiments, the exciter antenna(s) is/are driven by a conventional oscillator and power amplifier at a level sufficient to power the tag(s). In some embodiments, the implanted tag amplitude-modulates (AM's) the continuous wave (CW) carrier power from the exciter, thus emitting sidebands at frequencies defined by a number programmed into the tag's counter. In some embodiments, these sidebands, as well as the much stronger CW carrier, are ultimately detected by the third component.

In some embodiments, the tag comprises a self-resonant object (e.g., a small ferrite core with a wound inductor). The wound inductor possesses inter-winding capacitance that in combination with the inductance produces a high frequency resonant circuit. In some embodiments, the tag comprises a resonant object (e.g., the self-resonant object is equipped with a chip capacitor to produce resonance at a prescribed frequency). In some embodiments, the tag comprises a resonant or self-resonant object with a diode. A diode in combination with an LC circuit produces a sub-harmonic frequency when immersed in a magnetic field of sufficient strength (imposed voltage exceeds the diode's band-gap potential). In some embodiments, the tag comprises a resonant object or self-resonant object with an active modulator (e.g., integrated circuit amplitude modulates resonant circuit). In some embodiments, detection occurs similar to a full duplex (FDX) radio frequency identification (RFID) except that the modulation pattern is a simple sub-harmonic rather than a coded binary pattern; in some embodiments, the detection occurs after excitation similar to a half-duplex (HDX) mode of operation.

In some embodiments, the tag is configured for single-use. In some such embodiments, a tag can be disabled or deactivated (e.g., like an EAS tag). This is particularly useful where multiple tags are used in a procedure where individual tags are turned off to make detection of other tags easier (e.g., to avoid or reduce interference between multiple tags). In some embodiments, a burst of energy from an external device is used to disable or deactivate a tag. In other embodiments, the tag has an internal control component that, upon receiving instruction from an external device, turns the tag on or off (e.g., the tag stops "talking" temporarily or permanently).

In some embodiments, the tag has an exterior length, width, and depth, wherein the length is 30 mm or less (e.g., 20 mm or less, . . . , 10 mm or less, . . . , 9 mm or less, . . . , 8 mm or less, . . . , 5 mm or less, . . . , 3 mm or less, . . . , etc.), the width is 5 mm or less (e.g., 4 mm or less, . . . , 3 mm or less, . . . , 2 mm or less, . . . , 1 mm or less, . . . 0.5 mm or less, . . . , etc.), and the depth is 5 mm or less (e.g., 4 mm or less, . . . , 3 mm or less, . . . , 2 mm or less, . . . , 1 mm or less, . . . 0.5 mm or less, . . . , etc.).

In some embodiments, the tag is contained in a housing. In some embodiments, no housing is employed. In some embodiments, the housing comprises a biocompatible material. In some embodiments, the housing provides a liquid and/or gas resistant barrier separating the signal source from the exterior of the housing. In some embodiments, the housing is small, permitting administration of the tag through a needle, cannula, endoscope, catheter, or other medical device. In some such embodiments, the housing has an exterior length, width, and depth, wherein the length is 30 mm or less (e.g., 20 mm or less, . . . , 10 mm or less, . . . , 9 mm or less, . . . , 8 mm or less, . . . , 5 mm or less, . . . , 3 mm or less, . . . , etc.), the width is 5 mm or less (e.g., 4 mm or less, . . . , 3 mm or less, . . . , 2 mm or less, . . . , 1 mm or less, . . . 0.5 mm or less, . . . , etc.), and the depth is 5 mm or less (e.g., 4 mm or less, . . . , 3 mm or less, . . . , 2 mm or less, . . . , 1 mm or less, . . . 0.5 mm or less, . . . , etc.). The housing can be of any desired shape. In some embodiments, the housing is cylindrical along the length axis. In some embodiments, the housing is shaped like a grain of rice (e.g., cylindrical with rounded ends). In some embodiments, the housing is shaped like a pillar (e.g., cylindrical with flat ends). In some embodiments, the housing is polygonal along the length axis (e.g., triangular, square, rectangular, trapezoidal, pentagonal, etc., in cross-section). In some embodiments the housing has struts or other fasteners to keep the tag in place, avoiding migration in tissue. These struts may deploy upon placement in tissue. In some embodiments the fastener may be a biocompatible material that bonds with surrounding tissue.

In some embodiments, the housing is a single uniform component synthesized around the interior components of the tag. In other embodiments, the housing is made of two or more separate segments that are sealed together after introduction of the interior components of the tag. In some embodiments, the tag is completely or partially covered in a coating. In some embodiments, the coating comprises a biocompatible material (e.g., parylene-C, etc.).

In some embodiments, the tag does not comprise any power source. For example, in some embodiments, the signal is generated from the signal source in response to a magnetic field as the activation event (i.e., electromagnetic induction).

In some embodiments, the tag comprises a radio-frequency identification (RFID) chip (e.g., in a housing). In some embodiments, the RFID chip comprises a radio-frequency electromagnetic field coil that modulates an external magnetic field to transfer a coded identification number and/or other coded information when queried by a reader device. In some embodiments, the RFID chip collects energy from an EM field generated by the second component (or other device) and then acts as a passive transponder to emit microwaves or UHF radio waves. In some embodiments, the RFID chip is read-only. In other embodiments, it is read/write. The technology is not limited by the nature of the information provided by the RFID chip. In some embodiments, the information includes a serial number, lot or batch number, time information (e.g., production date; surgery date; etc.); patient-specific information (e.g., name, family history, drugs taken, allergies, risk factors, procedure type, gender, age, etc.); procedure-specific information; etc. The technology is not limited by the frequency used. In some embodiments, the RFID frequency is in the 120-150 kHz band (e.g., 134 kHz), the 13.56 MHz band, the 433 MHz band, the 865-868 MHz band, the 902-928 MHz band, the 2450-5800 MHz band, or the like. In some embodiments, the RFID chip is incorporated with browser-based software to increase its efficacy. In some embodiments, this software allows for different groups or specific hospital staff, nurses, and patients to see real-time data relevant to the tag, procedure, or personnel. In some embodiments, real-time data is stored and archived to make use of historical reporting functionality and to prove compliance with various industry regulations. In some embodiments, the RFID chip reports sensor data (e.g., temperature, movement, etc.). In some embodiments, the RFID chip contains or collects information that is read at a later time (e.g., after surgery). In some embodiments, information is reviewed during surgery. For example, a message may be provided to the surgeon (e.g., "the chip is just to the left of the tumor") to assist in guiding the surgeon (e.g., optimizing removal of a tumor with the appropriate margins).

In some embodiments, the tag consists of or consists essentially of the signal source and the housing or the signal source, the housing, and the RFID chip. In some embodiments, the tag (e.g., via the chip) emits an ultrasound signal (e.g., gray scale, spectral, or color Doppler) such that the signal is detectable by an ultrasound probe or a hand-held Doppler unit.

In some embodiments, a tag is heated during a procedure (e.g., via exposure to an external energy source). In some such embodiments, heating may be used to assist in coagulation or precoagulation of tissue or to provide thermotherapy (see e.g., U.S. Pat. Publ. No. 2008/0213382, herein incorporated by reference in its entirety). Heating may also be used to improve the efficacy of radiation therapy.

In some embodiments, the second component provides a remote activating device having one or more excitation coils (e.g., exciter assembly shown in FIG. 4A). In some embodiments, the excitation coils are provided in a patch or pad that is placed on the patient or on the operating table, although it can be positioned in any desired location within functional distance of the tags. In some embodiments, the remote activating device provides an AC magnetic field originating from one or more exciter antennas. In some embodiments, where the system is used to locate breast tumors, the patch encircles the treated breast or is placed otherwise near the breast. Similar approaches may be used for other targeted areas of a body. In some embodiments, a pad containing the excitation coil(s) are placed beneath the patient. In such embodiments, a large coil or multiple coils are employed. The excitation coil(s) may comprise or consist of several turns of a flat conductor patterned on a dielectric substrate, or may comprise or consist of magnet wire wound around a suitable mandrel; the coil is powered by an external frequency source, and the magnetic field emanating from the coil penetrates the patient's body to excite the tag, whose emissions are detected by a detection component.

In some embodiments, the excitation coil or coils are contained in a belt that is placed around the subject or a portion of the subject. In some embodiments, the external excitation coil may further be used for other aspects of the patient care, such as for radiotherapy or to act as a ground current return pad used in electrosurgery. In some embodiments, the remote activating device emits light (e.g., laser light). In some embodiments, the remote activating device is configured for single use (e.g., is disposable).

In some embodiments, the remote activating device employs an unmodulated constant frequency activation (i.e., the activation signal has constant amplitude and frequency). In some embodiments, the remote activating device employs an unmodulated swept frequency (i.e., the activation signal has constant amplitude and swept frequency between two endpoints). Such devices find use with resonant-type tags such that a detectable change in the activation signal's amplitude occurs when the transmitted frequency coincides with the tag's resonant frequency. In some embodiments, the remote activating device employs a pulsed frequency (i.e., the activation signal comprises brief excitation pulses at a periodic frequency, which may be comprised of two closely-related frequencies whose sum or difference is the response frequency of the tag). The pulsed activation produces a post-pulse sinusoidal decay signal. A tag alters the characteristic of the decaying signal, either in amplitude or time.

In some embodiments, the remote activating device comprises a hand-held component. In some embodiments, the hand-held component is lightweight to allow a surgeon to hold and manipulate the component over the course of a procedure (e.g., 5 kg or less, 4 kg or less, 3 kg or less, 2 kg or less, 1 kg or less, 0.5 kg or less, 0.25 kg or less, or any range therein between, e.g., 0.5 to 5 kg, 1 to 4 kg, etc.). In some embodiments, the hand-held component is shaped like a wand, having a proximal end that is held by the physician and a distal end that is pointed towards the treated subject or tissue harboring the tag. In some embodiments, the hand-held component is shaped like an otoscope, having a distal end that terminates at an angle (e.g., right angle) from the body of the component. In some embodiments, the remote activating device comprises an antenna that generates a magnetic field. In some embodiments, the remote activating device has only a single antenna (i.e., is monostatic). In some embodiments, the remote activating device has only two antennas (i.e., is bistatic).

In some embodiments, the magnetic field of the remote activating device (e.g., exciter assembly shown in FIG. 4A) is controlled by a processor running a computer program. In some embodiments, the remote activating device comprises a display or user interface that allows the user to control the remote activating device and/or monitor its functions while in use. In some embodiments, the remote activating device provides a visual, audio, numerical, symbol (e.g., arrows), textual, or other output that assists the user in locating the tag or identifying the distance to or direction of the tag from the remote activating device.

In some embodiments, the plurality of witness coils of the third component collectively provide several antennas at multiple defined locations relative to the tags and configured to receive a signal generated by the one or more tags upon being exposed to the magnetic field generated by the second component.

In some embodiments, each witness coil feeds a receiver channel, which is time-division multiplexed (TDM'd) to reduce the receiver complexity. Fixed witness stations of defined locations relative to the tag and each other (e.g., arrayed along the patient) contain one or more (e.g., one to three) witness coils arranged in a locally orthogonal manner to sense various components of the AC magnetic field from the tag. In some embodiments, one or more or all of these witness coils in the witness stations is also TDM'd into a receiver channel, reducing complexity, as well as cross-talk between antennas.

In some embodiments, witness coils comprise or consist of a ferrite-loaded cylindrical coil antenna, tuned (e.g., with one or more capacitors in parallel) for resonance at the frequency of an exciter (e.g., tag or emitter), (e.g., 100-200 kHz). Typical dimensions of a witness coils are 3-5 mm diameter and 8-12 mm length, although both smaller and larger dimensions may be employed.

In some embodiments, the witness stations are provided below the patient (e.g., in a pad, garment, or other device positioned below the patient). In some embodiments, the witness stations are integrated into a surgical table or imaging device in which a patient is placed during a medical procedure. In some embodiments, the witness stations are placed on the floor, wall, or ceiling of the operating room or in a medical transport vehicle. In some embodiments, the witness stations are integrated into or attached to a medical device used in the medical procedure.

In some embodiments, a fourth component provides a medical device location emitter in an attachment component (see FIGS. 9-12) to allow the system to determine the location, position, distance, or other characteristic of a medical device relative to the tag or tags. In some embodiments, the medical device location emitter or emitters are integrated into a medical device or into an attachment component. In other embodiments, they are attachable to a medical device. In some such embodiments, the location emitters are provided in an attachment component (e.g., sleeve) that slips over a portion of a medical device. The location emitters may operate as and/or comprise the same materials as the tags, but are positioned on or near a medical device rather than within tissue. For example, in some embodiments, the emitters comprise coils that are excited with both carrier and/or sidebands, enabling the emitters to emit signals as though it were a tag. In other embodiments, the location emitters are wired to a power and signal source.

In some embodiments, location of the location emitters is accomplished geometrically by measuring the quasi-simultaneous power detected from the emitters at a plurality of witness stations (e.g., four or more stations), and using the power differences to perform vector math that determines the location of the emitter without ambiguity. This process is facilitated by a preliminary calibration using a known tag in a known location prior to the procedure.

Vectors describing the location of the location emitters are used to provide visualization guidance to the surgeon about the spatial relationship of a medical device (e.g., particularly its tip) to an implanted tag, or (e.g., with computational guidance) to a lesion boundary. Use of multiple location emitters on an attachment component attached to a medical device provides vectors to determine the device's principal axis using the same vector math. Where a more complex medical device, such as a robotic surgical system (e.g., da Vinci surgical system) is employed, multiple location emitters located on multiple different locations of the device are employed to provide location, orientation, and other position information of multiple components (e.g., arms) of the device. In some embodiments, the location emitters are also used as detectors (e.g., provide witness stations on the medical device).

In some embodiments, a fifth component provides one or more computing systems comprising one or more computer processors and appropriate software to analyze, calculate, and display tag and emitter position information (see, part 210 in FIG. 4A). In some embodiments, the display provides a graphical representation of the tag, patient, and/or medical device on a monitor. In other embodiments, the display provides directional information for moving or positioning the medical device. In some embodiments, the system automatically (e.g., robotically) controls the medical device or one or more functions thereof. In some embodiments, the display integrates tag and/or medical device information with previously obtained or concurrently obtained medical images of the patient or target tissue (e.g., CT, Mill, ultrasound, or other imaging modalities). For example, in some embodiments, an image indicating a tag or tags is fused with an image of the subject's tissue or body region obtained from an imaging device. In some embodiments, information is analyzed in real-time. In some embodiments, information is analyzed at one or more discrete time points.

In some embodiments, the fifth component provides command and control functions for a user of the system. In some embodiments, the fifth component has information stored thereon that helps guide the information displayed on the attachment component. For example, the information may include data on the type of medical device the attachment component is attached to, or what tip or cutting implement is being used with a particular medical device. In this regard, the precise location of the cutting tip of a medical device and its relation to the tag (e.g., distance to the tag) is communicated to the surgeon (e.g., for very precise instructions on cutting tissue). Such information is, for example in some embodiments, manually entered into a control unit or attachment component by the user, or automatically found (e.g., by a barcode or other indicator) when a detection component is attached to a particular medical device.

The system finds use with a wide variety of medical devices and procedures. In some embodiments, the surgical device comprises an electrical surgical device that is turned on and off by a user, wherein a control unit that is part of the fifth component allows the remote activating device to generate the magnetic field when the electrical surgical device is off, and prevents the remote activating device from generating the magnetic field when the electrical surgical device is on (e.g., ensuring that the surgical device and detection system do not interfere with one another). In other embodiments, the surgical device comprises a power cord, wherein an AC current clamp is attached to the power cord, wherein the AC current clamp is electrically-linked or wirelessly linked to the control unit, wherein the AC current clamp senses when the electrical surgical device is on or off and reports this to the control unit (e.g., such that the control unit can ensure that the magnetic field from the surgical device and from the remote activating device are not active at the same time).

In certain embodiments, the surgical device comprises an electrocautery device, a laser cutting device, a plasma cutting device, or a metal cutting device (e.g., a surgical device manufactured by BOVIE MEDICAL). Additional examples of medical devices that find use in embodiments of the system are found, for example, in the following U.S. Pat. Nos. 9,144,453; 9,095,333; 9,060,765; 8,998,899; 8,979,834; 8,802,022; 8,795,272; 8,795,265; 8,728,076; 8,696,663; 8,647,342; 8,628,524; 8,409,190; 8,377,388; 8,226,640; 8,114,181; 8,100,897; 8,057,468; 8,012,154; 7,993,335; 7,871,423; 7,632,270; 6,361,532; all of which are herein incorporated by reference in their entireties, and particularly with respect to the hand-held medical devices disclosed therein.

In some embodiments, the attachment component has thereon, or attached thereto, a display component for directing the surgeon to the tag or tags. In some embodiments, the display component provides: i) a spatial orientation indicator (e.g., visual, audible, etc.), and/or ii) a distance-to-tag indicator (e.g., visual, audible, etc.). In some embodiments, the display component comprises a first display for presenting distance to tag information (e.g., visual, audible, lights, color, vibration, tactile, etc.), a second display for presenting vertical axis orientation, such as a preset preferred angle for approaching a tag in a patient (e.g., a visual, audible, lights, colors, vibration, tactile, etc. display); and/or a third display for presenting horizontal orientation (e.g., left to right information so the surgical device can be centered when approaching the tag). In some embodiments, the display component comprises a plurality of displays (e.g., visual, audible, sensory, etc.) that allow the correct pitch and yaw axes to be employed (to minimize non-target tissue damage), and/or further a display that provides distance to tag information. In certain embodiments, the medical device is moved around the patient's body prior to surgery to orient the emitters and the display component. In certain embodiments, a series of lights and/or sounds is provided on the display component that guides the surgeon (e.g., the surgeon attempts to keep the lights in a center of an "X" series of lights, and/or to keep the volume of warning sounds off or as low as possible).

The tag is not limited to placement within a particular body region, body part, organ, or tissue. For example, in some embodiments, the tag is placed in the cephalic, cervical, thoracic, abdominal, pelvic, upper extremities, or lower extremities region of the body. In some embodiments, the tag is placed within an organ system, such as the skeletal system, muscular system, cardiovascular system, digestive system, endocrine system, integumentary system, urinary system, lymphatic system, immune system, respiratory system, nervous system or reproductive system. In some embodiments, the tag is placed within an organ. Such organs may include the heart, lungs, blood vessels, ligaments, tendons, salivary glands, esophagus, stomach, liver, gallbladder, pancreas, intestines, rectum, anus, hypothalamus, pituitary gland, pineal gland, thyroid, parathyroids, adrenal glands, skin, hair, fat, nails, kidneys, ureters, bladder, urethra, pharynx, larynx, bronchi, diaphragm, brain, spinal cord, peripheral nervous system, ovaries, fallopian tubes, uterus, vagina, mammary glands, testes, vas deferens, seminal vesicles, and prostate. In some embodiments, the tag is placed within tissues, such as connective, muscle, nervous, and epithelial tissues. Such tissues may include cardiac muscle tissue, skeletal muscle tissue, smooth muscle tissue, loose connective tissue, dense connective tissue, reticular connective tissue, adipose tissue, cartilage, bone, blood, fibrous connective tissue, elastic connective tissue, lymphoid connective tissue, areolar connective tissue, simple squamous epithelium, simple cuboidal epithelium, simple columnar epithelium, stratified epithelium, pseudostratified epithelium, and transitional epithelium.

In some embodiments, the tissue region where the tag is located comprises a lesion. In some embodiments, the lesion is a tumor or a tissue region identified as being at risk for forming a tumor. In some embodiments, the lesion is fibrotic tissue. In some embodiments, the lesion is an inflamed or infected region. In some embodiments, the tag is placed within a lumen to detect function or other process of the organ or provide localizing information. For example, the tag could be swallowed, or placed into a hollow organ via endoscopy. In some embodiments, the tissue region is healthy tissue.

In some embodiments, the tag is placed within a solid tumor. Examples of solid tumors into which the tag may be placed include carcinomas, lymphomas, and sarcomas, including, but not limited to, aberrant basal-cell carcinoma, acinar cell neoplasms, acinic cell carcinoma, adenocarcinoma, adenoid cystic carcinoma, adenoid/pseudoglandular squamous cell carcinoma, adnexal neoplasms, adrenocortical adenoma, adrenocortical carcinoma, apudoma, basal cell carcinoma, basaloid squamous cell carcinoma, carcinoid, cholangiocarcinoma, cicatricial basal-cell carcinoma, clear cell adenocarcinoma, clear cell squamous-cell carcinoma, combined small cell carcinoma, comedocarcinoma, complex epithelial carcinoma, cylindroma, cystadenocarcinoma, cystadenoma, cystic basal-cell carcinoma, cystic neoplasms, ductal carcinoma, endometrioid tumor, epithelial neoplasms, extramammary Paget's disease, familial adenomatous polyposis, fibroepithelioma of Pinkus, gastrinoma, glucagonoma, Grawitz tumor, hepatocellular adenoma, hepatocellular carcinoma, hidrocystoma, Hurthle cell, infiltrative basal-cell carcinoma, insulinoma, intraepidermal squamous cell carcinoma, invasive lobular carcinoma, inverted papilloma, keratoacanthoma, Klatskin tumor, Krukenberg tumor, large cell keratinizing squamous cell carcinoma, large cell nonkeratinizing squamous cell carcinoma, linitis plastica, liposarcoma, lobular carcinoma, lymphoepithelial carcinoma, mammary ductal carcinoma, medullary carcinoma, medullary carcinoma of the breast, medullary thyroid cancer, micronodular basal-cell carcinoma, morpheaform basal-cell carcinoma, morphoeic basal-cell carcinoma, mucinous carcinoma, mucinous cystadenocarcinoma, mucinous cystadenoma, mucoepidermoid carcinoma, multiple endocrine neoplasia, neuroendocrine tumor, nodular basal-cell carcinoma, oncocytoma, osteosarcoma, ovarian serous cystadenoma, Paget's disease of the breast, pancreatic ductal carcinoma, pancreatic serous cystadenoma, papillary carcinoma, papillary hidradenoma, papillary serous cystadenocarcinoma, papillary squamous cell carcinoma, pigmented basal-cell carcinoma, polypoid basal-cell carcinoma, pore-like basal-cell carcinoma, prolactinoma, pseudomyxoma peritonei, renal cell carcinoma, renal oncocytoma, rodent ulcer, serous carcinoma, serous cystadenocarcinoma, signet ring cell carcinoma, signet-ring-cell squamous-cell carcinoma, skin appendage neoplasms, small cell carcinoma, small cell keratinizing squamous cell carcinoma, somatostatinoma, spindle cell squamous cell carcinoma, squamous cell carcinoma, squamous cell lung carcinoma, squamous cell thyroid carcinoma, superficial basal-cell carcinoma, superficial multicentric basal-cell carcinoma, syringocystadenoma papilliferum, syringoma, thymoma, transitional cell carcinoma, verrucous carcinoma, verrucous squamous cell carcinoma, VIPoma, and Warthin's tumor.

In some embodiments, placing the tag comprises the steps of inserting an introduction device into the subject and introducing the tag through the introduction device into the subject. In some embodiments, the introduction device is a needle, cannula, or endoscope. In some embodiments, the tag is forced through the introduction device (e.g., via physical force, pressure, or any other suitable technique) and released into the subject at the distal end of the introduction device. After the tag is placed, the introduction device is withdrawn, leaving the tag at the desired location with the subject. In some embodiments, the introduction of the tag is guided by imaging technology.

In some embodiments, multiple tags are placed into the subject. The tags may be of identical type or may differ (e.g., differ in signal type). The tags may be placed in proximity to one another or at distant locations. Multiple tags are used, in some embodiments, to triangulate the location intended for medical intervention.

In some embodiments, the tags are further used as fiducials for radiotherapy (or other targeted therapy). The location of the tags is identified with an external reader and used to place, for example, laser light on the skin surface exactly where the chip is located. This eliminates the need to use X-ray, CT, or fluoroscopy to see the fiducials. This also decreases or eliminates the need to put skin markers (e.g., tattoos) on patients. This also helps in respiratory compensation as the fiducial moves up and down with a tumor in the lung or abdomen. Therefore, one can conduct real-time radiation only when the tumor is in the correct position and decrease damage to the background tissue (e.g., avoid burning a vertical stripe in the patient as the tumor moves up and down). The use as fiducials for director therapy (e.g., radiation therapy) also enhances triangulation as depth information (based on signal strength) assists in localization of the tumor to minimize collateral damage.

In some embodiments, provided herein are systems and methods employing one or more or all of: a) a tag (e.g., comprising an antenna; e.g., a coil antenna; e.g., a ferrite-core coil antenna; e.g., that resonates at 100-200 kHz; e.g., coupled to an integrated circuit); b) a remote activation device that generates a magnetic field within a region of the tag; and c) a plurality of witness stations, each of the witness stations comprising an antenna configured to detect information generated by said tag or a change in a magnetic field generated by the remote activation device caused by said tag. In some embodiments, the tag emits sidebands at defined frequencies upon activation by a magnetic field and the witness stations detect such sidebands. In some embodiments, the tag emits the sidebands at frequencies defined by a number programmed into a counter in the tag.

In some embodiments, the remote activating device comprises an excitation coil that is, for example, powered by a generator electrically connected to the remote activating device. In some embodiments, the remote activating device comprises a pad configured to be placed in proximity to (e.g., under, above, beside) a patient having the tag embedded in the patient. In some embodiments, the pad also contains the witness stations.

Any number of other tag designs may be employed. In some embodiments, the tag comprises or consists of a ferrous pellet or particle. When the ferrous object is introduced within a magnetic field, the object creates an irregularity in the alternating magnetic field which is detectable by sense coils contained within witness stations, producing a phase and amplitude shift from null. The null is restored when the ferrous object is physically equidistant to two sense coils.

In some embodiments, the tag comprises a self-resonant object (e.g., a small ferrite core with a wound inductor). The wound inductor possesses inter-winding capacitance that in combination with the inductance produces a high frequency resonant circuit. Detection occurs, for example, using the approach described above for the ferrous pellet or, for example, using a Grid Dip Oscillator (GDO). The GDO has a resonant circuit that radiates an electromagnetic field. When proximal to the self-resonant object of the same frequency, power transfer from the GDO to the self-resonant object induces a detectable change in the GDO power. In some embodiments, the tag comprises a resonant object (e.g., self-resonant object is equipped with a chip capacitor to produce resonance at a prescribed frequency). In some embodiments, the tag comprises a resonant or self-resonant object with a diode. A diode in combination with LC circuit produces a sub-harmonic frequency when immersed in a magnetic field of sufficient strength (imposed voltage exceeds the diode's band-gap potential). In some embodiments, the tag comprises a resonant object or self-resonant object with an active modulator (e.g., integrated circuit amplitude modulates resonant circuit). Detection occurs similar to a full duplex (FDX) radio frequency identification (RFID) except that the modulation pattern is a simple sub-harmonic rather than a coded binary pattern.

In some embodiments, each witness antenna comprises or consists of a ferrite-loaded cylindrical coil antenna, tuned (e.g., with one or more capacitors in parallel) for resonance at the frequency of an exciter (e.g., tag or emitter) (e.g., typically 100-200 kHz). Typical dimensions of a witness antenna are 3-5 mm diameter and 8-12 mm length, although both smaller and larger antenna may be employed. In some embodiments, witness station antenna has a ferrite core size of 0.25×1 inch and contains 75-80 turns of a 10/46 (10 strands of #46) Litz wire which provides 0.157 mH (Q=53) (75 Turns).

In some embodiments, each witness coil is symmetrically wound about a ferrite core and connected to the secondary of a small balun transformer through two series capacitances, one for each wire from the coil. The total series capacitance is selected to resonate with the inductance of the coil, and the turns ratio of the balun transformer may be chosen to match the real impedance of the resonant coil/capacitor circuit to the transmission line, typically 50 Ohms. The real impedance of the resonant coil/capacitor circuit is typically 10 to 25 Ohms but may vary from just a couple Ohms to greater than 50 Ohms and may be adequately matched by appropriate choice of balun transformer primary and secondary turns. In addition to its role as impedance transformer, the balun minimizes any electric field generation/susceptibility from the witness coil assembly; alternately, it may be thought of as removing common mode effects.

In some embodiments, each witness station contains 1-3 witness antennas oriented orthogonally to each other and further arranged to have minimum cross-talk (i.e., interference with one another). The component housing the witness stations further comprises one or more receiver channels for collecting information obtained by the antennas of the witness stations. In some embodiments, the receiver comprises or consists of one or more channels, each channel fed by one or more (via a multiplexing switch) witness antennas.

The component (e.g., attachment component) that contains the location emitters may further comprise a display to assist the user in directing the medical device to the tag during a surgical procedure. In some such embodiments, a visual or audio display is provided on or associated with the medical device that receives location information about the tag from the computer system. The display may be one or more directional indicators such as LEDs, that indicate direction and/or distance to the tag. Color changes may be employed to indicate "on target" versus "off target" positions. In certain embodiments, the display comprises a first display for presenting distance to tag information (e.g., visual, audible, lights, color, vibration, tactile, etc.); a second display for presenting vertical axis orientation, such as a preset preferred angle for approaching a tag in a patient (e.g., a visual, audible, lights, colors, vibration, tactile, etc. display); and/or a third display for presenting horizontal orientation (e.g., left to right information so the surgical device can be centered when approaching the tag). In some embodiments, the display comprises a plurality of displays (e.g., visual, audible, sensory, etc.) that allow the correct pitch and yaw axes to be employed (to minimize non-target tissue damage), and/or further a display that provides distance to tag information. In certain embodiments, a series of lights and/or sounds are provided on the display that guide the surgeon (e.g., the surgeon attempts to keep the lights in a center of an "X" series of lights, and/or to keep the volume of warning sounds off or as low as possible).

The technology is not limited by the mode of tag placement and a wide variety of placements techniques are contemplated including, but not limited to, open surgery, laparoscopy, endoscopy, via endovascular catheter, etc. The tags may be placed by any suitable device, including, but not limited to, syringes, endoscopes, bronchoscopes, extended bronchoscopes, laparoscopes, thoracoscopes, etc. An exemplary protocol is provided below.

A patient previously identified as having a breast tumor is admitted to a medical facility. The patient is initially sent to radiology. The radiologist examines prior imaging information identifying the target tumor. The subject is administered a local anesthetic, usually lidocaine or a derivative, using a needle introduced percutaneously. The subject is positioned in an imaging device, generally either ultrasound, conventional mammography, or a stereotactic unit. The location of the tumor is determined. An introducer needle (usually 6-20 gauge) is inserted either into or just proximal to the tumor and a biopsy needle is placed through the introducer needle and a specimen is obtained using a variety of methods (suction, mechanical cutting, freezing to fix the position of the tissue followed by mechanical cutting). After the specimen is obtained and sent for pathologic examination, a 6-20 gauge tag delivery needle is inserted into the coaxial introducer needle to the tissue with the distal open end positioned at the lesion. A tag is inserted into the proximal end of the delivery needle and delivered by plunger through the opening at the distal end of the needle and into the tissue. Likewise, the tag could have been pre-positioned at the distal end of the delivery needle. Proper location of the tag is confirmed via imaging. The delivery needle is withdrawn, leaving the tag in place in the breast tissue.

This type of procedure can be performed in an analogous manner in virtually any body space, organ, or pathologic tissue with the intent of localizing that tissue or space for further diagnosis or treatment of any kind. Areas of particular interest include but are not limited to the following organs, and disease processes that take place within them: brain, skull, head and neck, thoracic cavity, lungs, heart, blood vessels, gastrointestinal structures, liver, spleen, pancreas, kidneys, retroperitoneum, lymph nodes, pelvis, bladder, genitourinary system, uterus, ovaries, and nerves.

In some embodiments, during surgery, the patient is placed onto an operating table with the surgical area exposed and sterilized. The surgeon is provided with the imaging information showing the location of the target tissue (e.g., tumor) and tag. An incision is made at the location of the entry point of the placement needle. The remote activating device is placed in proximity to the tissue to activate the tag. The detection component comprising the witness stations (e.g., as shown in FIG. 4A) detects a signal from the tag and allows the surgeon to guide the direction of the medical device toward the tumor. Once the tumor is localized, the surgeon removes the appropriate tissue and, optionally, removes the tag.

In some embodiments, the system finds use in surgery with the tags placed as fiducials on or in the body. The relative position of the tags and any surgical instruments is located using the electromagnetic field. This information is communicated to a physician in real-time using a variety of methods including by not limited to visual (computer screens, direction and depth indicators using a variety of methods, haptic feedback, audio feedback, holograms, etc.), and the position of the instruments displayed on any medical images such as CT, MRI, or PET scans in 2D or 3D. This data finds use to guide the physician during a procedure, or is used as a training method so that physicians can perform a virtual procedure. Such system may be integrated into or provide alternative approaches to existing surgical systems, such as the STEALTH system (Medtronic) for applications such as neurosurgeries.

In some embodiments, information about the location of the tag or tags or the surgical paths or routes to the tags is conveyed to a surgeon or other user in a manner that comprises one or more augmented reality or virtual reality components. For example, in some embodiments, a surgeon wears or accesses a virtual reality device (e.g., goggles, glasses, helmet, etc.) that shows a partial or complete virtual image of the patient or surgical landscape. Tag position information collected and calculated by the systems described herein are represented by one or more visual components to the surgeons to assist in accurate targeting of the tag or tags. For example, the tissue containing the tag may be represented with a virtual image of the tag location shown. Likewise, in some embodiments, a surgical pathway is visually presented, for example, as a colored line to be followed. In some embodiments employing augmented reality features, a display, presents a graphical or video capture of the patient representative of what the surgeon would visualize if the monitor were not present and overlays one or more augmented features on the display. The graphical or video display data may be captured by one or more cameras in the surgical field. The augmented features include, but are not limited to, a representation of the location of the tag in the target tissue, a projected surgical path, a target point to which the surgeon aligns the tip of the surgical device, a simulated surgical margin zone to treat, arrows or other location indicators that recommend movement if the optimal pathway is deviated from, or the like.

An exemplary exciter assembly 250 is shown in FIGS. 4, 5, 6, and 7. This exciter assembly, as shown in FIG. 1, can be positioned under the mattress of a patient lying on a surface, such as an operating table or mattress. The exemplary exciter assembly in these figures provides the excitation signal, via four exciter coils 150, for the tag(s) in the patient. The exemplary exciter assembly in FIG. 4A provides a plurality of witness coil assemblies (aka witness station assembly) 161, each with a witness coil 160, in order to detect the signal from implanted tag(s) and the tags in the attachment component that is attached to the surgical device. The exciter assembly is composed of a base substrate 140 to which other components are generally attached or integrated into. The base substrate is composed of any suitable material, which may be, for example, polycarbonate or the like and is typically nonmagnetic and non-electrically conducting. Not pictured in FIG. 4A is a top cover 230 (see FIG. 8) that mates with the base substrate, enclosing all the internal components therein. The top cover is composed of any suitable material, including Kevlar and/or other rigid materials, again typically nonmagnetic and non-electrically conducting. Foam or other type of padding may be included on top of the top cover.

Attached to the base substrate are four large exciter coils 150, which are labeled "Coil A," "Coil B," "Coil C," and "Coil D," in FIG. 4A. Each exciter coil 150 can be wound around four exciter coil mounts 155. In certain embodiments, the exciter coils are not wound in any particular form and instead employ wires that bond to themselves to create the coil shape. While not shown in FIG. 4A, in certain embodiments, coil covers (e.g., plastic coil covers) are situated over each of the four exciter coils. Between the four exciter coils, generally centrally located, is a large central balun circuit 180.

On the interior of exciter coils B, C, and D is a switch 190. The switch 190 contains a component, such as a relay or multiple PIN diodes (e.g., at least four PIN diodes), or filed effect transistor, that controls the directionality of the current (clockwise or counterclockwise) in the respective exciter coils. In the particular embodiment in FIG. 4A, excited Coil A does not have a switch 190 as the direction in this coil is not changed. The switch 190 is linked to difference capacitors employed to correctly match the different inductance resulting from changing the directionality of current flow. If a relay(s) (e.g., four SPST, two SPDT type or one DPDT) is employed in the switch, it generally directs an input to one of two outputs. If multiple PIN diodes are employed (to create relay function) in the switch 190, this provides a very high impedance when "off" and low impedance when "on." Each switch 190 also is linked to one or more capacitors to modify the capacitance that, along with the exciter coil inductor, forms the resonant circuit. This is necessary because the effective total series inductance of all exciter coils changes when the current flow direction is changed. Also on the interior of Coils A-D are a pair of capacitor assemblies 195, composed of a central capacitor 197, flanked by metal leads 199. In certain embodiments, the metal leads 199, are affixed to ceramic heat spreaders, in order to dissipate heat that builds up during operation.

In operation, the exciter assembly in FIG. 4A is configured, in certain embodiments, to cycle between three configurations, called Configuration 1 (shown in FIG. 5), Configuration 2 (shown in FIG. 6), and Configuration 3 (shown in FIG. 7). In Configuration 1, as shown in FIG. 5, the current from all four exciter coils is clockwise in order to simulate an exciter coil generally aligned with its plane normal to the Z axis. In Configuration 2, as shown in FIG. 6, the current from Coil A and Coil B is clockwise, while the current from Coil C and Coil D is counterclockwise, in order to simulate an exciter coil generally aligned to the Y axis. In configuration 3, as shown in FIG. 7, the current from Coil A and Coil C is clockwise, while the current from Coil B and Coil D is counterclockwise, in order to simulate an exciter coil generally aligned to the X axis. Although this is a preferred embodiment, other combinations of coil polarities with other values of additional series capacitance may be advantageous for certain tag orientations. For example, the current in coil A, instead of being clockwise, could be counterclockwise, and then all of the other 3 coils (Coils B, C, and D) could have the current flow as shown in FIG. 5, 6, or 7, or the other 3 coils (Coils B, C, and D) would have the opposite current flow as shown in FIGS. 5, 6, and 7. In other embodiments, the current arrangement is as shown in FIG. 6, except the current in Coil B is counterclockwise, and the current in Coil D is clockwise. Every different combination of clockwise and counterclockwise for the Coils A-D is contemplated (i.e., all sixteen combinations).

The exemplary exciter assembly 250 in FIG. 4A is also shown with twelve witness station assemblies 161 (each with a witness coil 160). The twelve witness coils 160 alternate opposite orientation (along x and y axes) to reduce crosstalk. In other embodiments, software may also or alternatively be used to reduce cross talk. In certain embodiments, rather than alternating orientation, all of the witness coils point toward the center, which would increase crosstalk, but may have the advantage of shifting the location of inflection points in the witness coil signal pickups as a beacon is transitioned across the perimeter of the exciter assembly. It is generally preferably for the wires that feed into the exciter coils not be in close proximity to any of the witness coils, to prevent reduction in isolation and noise pickup. In FIG. 4A, the wires from the center balun circuit to each of the four exciter coils are in a location away from the twelve witness coils 160. Also, as shown in FIG. 4A, the witness coils run down the left and right side of the exciter assembly, and do not run across the top or bottom of the exciter assembly. Adding witness stations across the top and/or bottom can cause strong crosstalk to occur. Alternatively, software applications can be used to reduce cross talk if witness coils are placed in positions that induce crosstalk. The witness coils 160 are held in place by a pair of witness coil brackets 165.

Next to each witness coil 160 is a printed circuit board 170. Each printed circuit board 170 contains capacitors and a small balun circuit. The capacitors, along with the witness coil, are employed to create a resonant circuit. The balun serves to eliminate common mode effects that would otherwise make the witness coil assembly susceptible to electric field interaction. It also may serve as an impedance matching element that matches the real impedance of the coil/capacitor resonant circuit to the transmission line characteristic impedance, typically 50 Ohms, by optimally selecting the number of primary and secondary turns.

The exciter assembly 250 in FIG. 4A is also shown with a pair of self-test emitters 220. These self-test emitters 220 are present such that one can apply known signals and check the response on all witness coils. If a witness coils does not show the expected signal, it indicates a system problem, or could indicate the presence of an interfering magnet or piece of metal which is distorting the field and degrading overall localization accuracy. It is noted that another self-test that can be employed is to generate a signal on the exciter coils that is normally applied to one of the emitters on the attachment component (e.g., sheath on hand held surgical device). By measuring the signal passed from the exciter to each witness coils, one can confirm the level of isolation between them. In still another self-test, a signal may be applied to each witness coil individually and the remaining witness coils may be used to detect the signal. In other embodiments, field witness coil crosstalk may also be measured this way and used to calibrate the system.

FIG. 4A shows various wire connections between the various components of the exciter assembly. Each witness coil 160 is attached to a coaxial cable which is connected to the system electronics enclosure (labelled "controller," 210) via the cable bundle 200. The exciter signal comes from the cable bundle 200 into the central balun circuit 180. From there, wires carry the signal to the switches 190 and/or capacitor assemblies 195. The system electronics enclosure (controller 210) performs signal processing (e.g., filtering, mixing, amplification, digitization, and demodulation of multiple frequency 'channels') on the witness coil signals. Generally, no A/C main power is applied to the witness coils.

In regard to the capacitors employed in each capacitor assembly 195, and in the printed circuit boards 170, in general, the capacitors are chosen to be COG/NPO type where the capacitance value does not change with temperature, so that the resonant frequency of the exciter does not change with temperature. The capacitors also provide a tuning network which can selectively add capacitance in series to change the resonant frequency, which helps reduce tolerances during manufacturing, as well as makes it more tolerant of tuning changes due to temperature and other factors. In general, all the materials employed should have high dielectric strength and high stability over temperature to prevent geometric changes as the exciter assembly is used and the temperature is raised.

An exemplary witness coil assembly (aka witness station assembly) 161 is shown in FIG. 4B. Witness coil assembly 161 includes witness coil two witness coil brackets 165, which are used to clamp an secure witness coil 160 against elastomer 162. The witness coil 160, as shown in FIGS. 4B and 4C, is composed of a metal core (e.g., ferrite core) 166 and coils 167 formed from wire. As shown in exemplary FIG. 4C, the metal core 166 is composed of a central region 173 (under the wires in FIG. 4C), with a wire-free proximal end 171 and a wire-free distal end 172. Only the ferrite core (using the proximal and distal ends that are wire-free) is clamped by bracket 165 and elastomer 162 (e.g., to provide best registration and eliminate the possibility of damaging the coil windings 167 of witness coil 160). The height of each end of witness coil 160 may be adjusted up or down by adjustment screws 163 (present in each witness coil bracket 165) while a restoring force is provided by elastomer 162. Elastomer thickness and durometer is chosen to provide the needed restoring force over the desired range of adjustment so that the adjustment screws will be easily adjusted yet hold the desired setting once the optimal position is achieved. Additionally, coil brackets 165 each has a "V" or "U" shaped feature that allows them to secure the proximal and distal ends of the metal core 166. This allows, for example, the brackets 165 to precisely register the witness coil core (e.g., ferrite core) in the desired direction so it cannot rotate about an axis perpendicular to the plane containing exciter coils. The witness coil assembly 161 also includes a printed circuit board 170 (with capacitors and balun circuit) and a faraday shield 168. The faraday shield may be composed of conductive material, such as brass or copper.

In certain embodiments, the exciter coil (e.g., as shown in FIG. 4A) is connected to port 1 of a vector network analyzer or VNA. The witness coil output is generally connected to port 2 of the VNA and transmission (S21) is measured and displayed. This measurement is a direct measurement of the signal present at port 2 resulting from excitation provided to port 1 and is, therefore, a direct measurement of isolation. The lower S21 (more negative) the better. The more negative S21 the better. Typical isolation values (S21) achieved with the generally preferred embodiment are −70 dB with usable ranges including −50 dB to more than −100 dB (e.g., the noise floor of the VNA).

In general, to achieve the best isolation between exciter coil and witness coil for the best accuracy over the largest navigation volume, it is generally important to position the witness coils orthogonal (e.g., precisely orthogonal) to the magnetic flux produced by the exciter coil. FIG. 4A shows such an orthogonal arrangement of the twelve witness coils. Small offsets to height or tilt of the witness coil from this optimal position will generally result in signal coupling to the witness coil from the exciter coil that undermines isolation. Accordingly, in certain embodiments, the screws (or other connectors) on the witness coil brackets are employed to make fine adjustments.

FIG. 4C shows an exemplary witness coil 160, including how the coils 167 are formed by wire being wound around the metal core in three stages: i) wind direction 1, where wire is wound around most of a first half of the metal core; ii) wind direction 2, where wire is wound over the top of the wire wound over the first half, as well as over most of the second half of the metal core; and iii) wind direction 3, where wire is wound back over the wire on the second half. In certain embodiments, 80-140 windings (e.g., 80 . . . 90 . . . 112 . . . 140) are on each half of the metal core (e.g., for total of 160-280 windings (e.g., 160 . . . 200 . . . 224 . . . 280). In certain embodiments, the wire is 32 AWG copper magnet wire with a single layer polyester enamel and bond coat (e.g., 0.011 inches in diameter), and heat is used during wrapping to secure wire wraps. In certain embodiments, the metal core is a ferrite core part number #4077484611 from FAIR-RITE products corporation. In certain embodiments, the metal core (e.g., ferrite core) has a diameter of about 10-15 mm (e.g., 10 . . . 12 . . . 14 . . . 15 mm), and is about 30-50 mm in length (e.g., 30 . . . 35 . . . 45 . . . 50 mm). In certain embodiments, the metal core has a diameter of about 12.7 mm and a length of about 41.5 mm.

The wire is also connected to the secondary of a small balun transformer (in the printed circuit board, part 170 in FIG. 4B) through two series capacitances (e.g., in the printed circuit board), one for each wire from the coil. In general, in certain embodiments, the total series capacitance is selected to resonate with the inductance of the coil in the tag, and the turns ratio of the balun transformer may be chosen to match the real impedance of the resonant coil/capacitor circuit to the transmission line (e.g., around 50 Ohms). In certain embodiments, the real impedance of the resonant coil/capacitor circuit is typically 10 to 25 Ohms, but may vary from just a couple Ohms to greater than 50 Ohms and may be adequately matched by appropriate choice of balun transformer primary and secondary turns. In addition to its role as impedance transformer, the balun minimizes any electric field generation/susceptibility from the witness coil assembly; alternately, it may be thought of as removing common mode effects. To further reduce the electric field susceptibility, the use of a conductive faraday shield 168 over the balun and capacitors is employed. This faraday shield (e.g., Faraday cage) reduces the observed electric field to components under the shield. Typically a Faraday shield is used to reduce the emission of electric fields of components under the shield, in this case it is also reducing the reception of electric fields.

FIG. 8 shows an emitter component 250 with the top cover 230 on. The top cover 230 may be composed of Kevlar or other suitably tough material. The exciter assembly 250 is shown with cable bundle 200 leading therein.

FIG. 9 shows an attachment component 10, with an angled distal end 300 that the distal tip 25 of the medical device 20 is inserted through. The display component 40 is attached to an attachment component control unit 310 via attachment component wire 60.

FIG. 10. Panel A shows the distal end 25 of a medical device 20 after it is initially inserted through the angled distal end 300 of attachment component 10. This view is prior to the attachment component wire 60 being inserted into the cable management component 315. Panel B shows attachment component wire 60 prior to being attached to the cable management component 315 of the display component housing 330. Panel B also shows the housing tapered connection 340 that the proximal end tapered connection 350 of the attachment component 10 is inserted into. The cable management component 315 has two clips that align both the attachment component wire 60 and the medical device wire 50.

FIG. 11 shows an attachment component 10 attached to a display component housing 330. The attachment component 10 has a pair of location emitters 70, which are linked to location emitter wires leads 72 which are inside tube 360. The location emitters 70 are powered by the wire leads 72 to generate a signal which is detected by the witness coils. The attachment component also has an angled distal end 300 with a distal end opening 305, which allows the tip of a medical or other device to be inserted therethrough. The display component housing 330 has a cable management component 315, composed of a pair of clips for holding the attachment component wire and the medical device wire.

FIG. 12 shows an exemplary attachment component 10 attached to a display component housing 330 with a display component 40 located therein. A display cover 370 is shown, which is used to secure the display component 40 inside the display component housing 330. Also shown is an adhesive strip 380 (e.g., a two sided strip with strong adhesive on both sides), which is shaped and sized to fit inside the attachment component and help secure a medical device to the attachment component.

FIG. 13. Panel A shows the proximal end tapered connection 350 of the attachment component 10, which is configured to push-fit into housing tapered connection 340 of the display component housing 330. Panel B shows a close up of section A of Panel A, including cable management tapered connection 317 that is part of cable management component 315 and designed to be inserted into tapered connection hole 319 of display component housing 330. Cable management tapered connection 317 includes a flat part 318 to lock angular position.

FIG. 14 shows an exemplary system for localizing a tag that is implanted in a patient. The system is composed of an exciter assembly that emits signals that activate the tags in the patient. A systems electronics enclosure is shown as a mobile cart, which delivers signals to the exciter assembly and receives and processes signals from the tag(s) in the patient and the location emitters in the attachment component. Guidance for a surgeon is displayed on the display component, as well as on a screen on the systems electronics enclosure.

We claim:
1. A device comprising:
   a) a base substrate,
   b) a plurality of exciter coils attached to said base substrate and configured to generate a magnetic field in three orthogonal directions for causing a tag to generate a signal, the plurality of exciter coils includes a first exciter coil, a second exciter coil, a third exciter coil, and a fourth exciter coil,
   c) a plurality of switches that control the direction of current through the plurality of exciter coils, and
   d) a plurality of witness station assemblies;
   wherein the second exciter coil is electrically coupled to a first capacitance when current through the second exciter coil is a first polarity, and wherein the second exciter coil is electrically coupled to a second capacitance, different than the first capacitance, when current through the second exciter coils is a second, opposite, polarity.

2. The device of claim 1, wherein each of the plurality of witness station assemblies comprises a witness coil, wherein said witness coil comprises:
   A) a metal core having a coil-free proximal end, a coil-free distal end, and a central region, and
   B) coil windings wound around said central region of said metal core.

3. The device of claim 2, wherein each of the plurality of witness station assemblies comprises a first witness coil bracket and a second witness coil bracket, and a first elastomeric part and a second elastomeric part,
   wherein said coil-free proximal end of said metal core is secured between said first witness coil bracket and said first elastomeric part, and
   wherein said coil-free distal end of said metal core is secured between said second witness coil bracket and said second elastomeric part.

4. The device of claim 3, wherein said first and second witness coil brackets each comprises at least one adjustment part.

5. The device of claim 1, wherein each of the plurality of switches comprises a relay element, a PIN diode, or a field effect transistor.

6. The device of claim 1, wherein each exciter coil comprises at least 50 turns and/or is composed of Litz wire.

7. The device of claim 1, further comprising a balun circuit electrically linked to the plurality of exciter coils.

8. The device of claim 1, further comprising a plurality of capacitors, wherein each of the plurality of switches is linked to at least one of the plurality of capacitors.

9. The device of claim 1, wherein said plurality of witness station assemblies collectively comprises a plurality of witness coils configured to detect said signal from said tag.

10. The device of claim 9, further comprising a plurality of printed circuit boards, wherein each of said plurality of witness coils is operably linked to one of said plurality of circuit boards.

11. The device of claim 10, wherein each of the plurality of circuit boards comprises at least two capacitors and at least one balun circuit.

12. The device of claim 1, wherein said each witness station assembly further comprises an electronics part electrically linked to said witness coil, wherein said electronics part comprises at least one capacitor and/or at least one balun circuit.

13. The device of claim 1, wherein said plurality of witness station assemblies further comprises a faraday shield.

14. The device of claim 1, wherein each of the plurality of witness station assemblies is positioned orthogonal to one of the three orthogonal magnetic fields.

15. The device of claim 1, wherein a resonant frequency of a series combination of first, second, third, and fourth exciter coils is adjusted with at least one capacitance.

16. The device of claim 1, wherein current in the first exciter coil travels in a clockwise direction when the magnetic field is generated in each of the three orthogonal directions.

17. The device of claim 16, wherein current in the second exciter coil travels in the clockwise direction, current in the third exciter coil travels in the clockwise direction, and current in the fourth exciter coil travels in the clockwise direction when the magnetic field is generated in one of the three orthogonal directions.

18. The device of claim 1, further including a plurality of tuning capacitors providing a tuning network to change a resonant frequency of the first, second, third, and fourth exciter coils.

19. A device comprising:
   a) a base substrate,
   b) a plurality of exciter coils attached to said base substrate and configured to generate a magnetic field in three orthogonal directions for causing a tag to generate a signal,
   c) a plurality of switches that control the direction of current through the plurality of exciter coils, and
   d) a plurality of witness station assemblies, wherein each of the plurality of witness station assemblies comprises a witness coil, wherein said witness coil comprises: a metal core having a coil-free proximal end, a coil-free distal end, and a central region, and coil windings wound around said central region of said metal core, and
   wherein each of the plurality of witness station assemblies comprises a first witness coil bracket and a second witness coil bracket, and a first elastomeric part and a second elastomeric part, wherein said coil-free proximal end of said metal core is secured between said first witness coil bracket and said first elastomeric part, and wherein said coil-free distal end of said metal core is secured between said second witness coil bracket and said second elastomeric part.

20. The device of claim 19, wherein said first and second witness coil brackets each comprises at least one adjustment part.

21. The device of claim 19, further comprising a balun circuit electrically linked to the plurality of exciter coils.

22. The device of claim 19, further including a plurality of capacitors providing a tuning network to change a resonant frequency of the plurality of exciter coils.

23. The device of claim 19, wherein the plurality of exciter coils includes a first exciter coil, a second exciter coil, a third exciter coil, and a fourth exciter coil, and wherein the second exciter coil is electrically coupled to a first capacitance when current through the second exciter coil is a first polarity, and wherein the second exciter coil is electrically coupled to a second capacitance, different than the first capacitance, when current through the second exciter coils is a second, opposite, polarity.

24. A device comprising:
   a) a base substrate,
   b) a plurality of exciter coils attached to said base substrate and configured to generate a magnetic field in three orthogonal directions for causing a tag to generate a signal; the plurality of exciter coils includes a first exciter coil, a second exciter coil, a third exciter coil, and a fourth exciter coil,
   c) a plurality of switches that control the direction of current through the plurality of exciter coils, and
   d) a plurality of witness station assemblies;
   wherein current in the first exciter coil travels in a clockwise direction when the magnetic field is generated in each of the three orthogonal directions; and
   wherein current in the second exciter coil travels in the clockwise direction, current in the third exciter coil travels in the clockwise direction, and current in the fourth exciter coil travels in the clockwise direction when the magnetic field is generated in one of the three orthogonal directions.

25. The device of claim 24, further including a plurality of capacitors providing a tuning network to change a resonant frequency of the first, second, third, and fourth exciter coils.

26. The device of claim 24, wherein each of the plurality of witness station assemblies comprises a witness coil, a bracket, and at least one adjustment part.

27. The device of claim 24, wherein the second exciter coil is electrically coupled to a first capacitance when current through the second exciter coil is a first polarity, and wherein the second exciter coil is electrically coupled to a second capacitance, different than the first capacitance, when current through the second exciter coils is a second, opposite, polarity.

* * * * *